United States Patent
Joshi et al.

(10) Patent No.: US 8,388,571 B2
(45) Date of Patent: Mar. 5, 2013

(54) FLUID DISPENSER WITH NON-ELECTRIC FLUID HEATING COMPONENT

(75) Inventors: Serena Joshi, San Francisco, CA (US); George N. Glavee, San Ramon, CA (US); Donald B. Bivin, Oakland, CA (US); Joshua W. Kriesel, San Francisco, CA (US); Marshall S. Kriesel, St. Paul, MN (US)

(73) Assignee: BioQuiddity, Inc., San Francisco, CA (US)

( * ) Notice: Subject to any disclaimer, the term of this patent is extended or adjusted under 35 U.S.C. 154(b) by 573 days.

(21) Appl. No.: 12/587,442

(22) Filed: Oct. 6, 2009

(65) Prior Publication Data

US 2011/0082422 A1    Apr. 7, 2011

(51) Int. Cl.
*A61M 37/00* (2006.01)
*A61M 5/30* (2006.01)
*A61F 7/12* (2006.01)

(52) U.S. Cl. .............. 604/85; 604/113; 604/70

(58) Field of Classification Search ............... 604/26, 604/82–92, 181–243, 113, 70
See application file for complete search history.

(56) References Cited

U.S. PATENT DOCUMENTS

| | | |
|---|---|---|
| 2,236,084 A | 3/1941 | Brown |
| 3,884,228 A | 5/1975 | Hahn |
| 5,009,251 A | 4/1991 | Pike et al. |
| 5,380,287 A | 1/1995 | Kikuchi et al. |
| 5,632,315 A | 5/1997 | Rose |
| 6,056,716 A | 5/2000 | D'Antonio et al. |
| 6,236,624 B1 | 5/2001 | Kriesel et al. |
| 6,355,019 B1 | 3/2002 | Kriesel et al. |
| 6,416,495 B1 | 7/2002 | Kriesel et al. |
| 2011/0082423 A1* | 4/2011 | Joshi et al. ............... 604/113 |

* cited by examiner

*Primary Examiner* — Nicholas D Lucchesi
*Assistant Examiner* — Pritesh Patel
(74) *Attorney, Agent, or Firm* — James E. Brunton

(57) ABSTRACT

A novel dispensing system for dispensing medicaments to a patient that includes means for controllably heating fluid medicaments within the dispensing system by converting a chemical component, such as calcium chloride or the like, into a solution or solvent by adding a suitable solution or solvent to create an exothermic process causing an increase in temperature of the mixed solution.

7 Claims, 24 Drawing Sheets

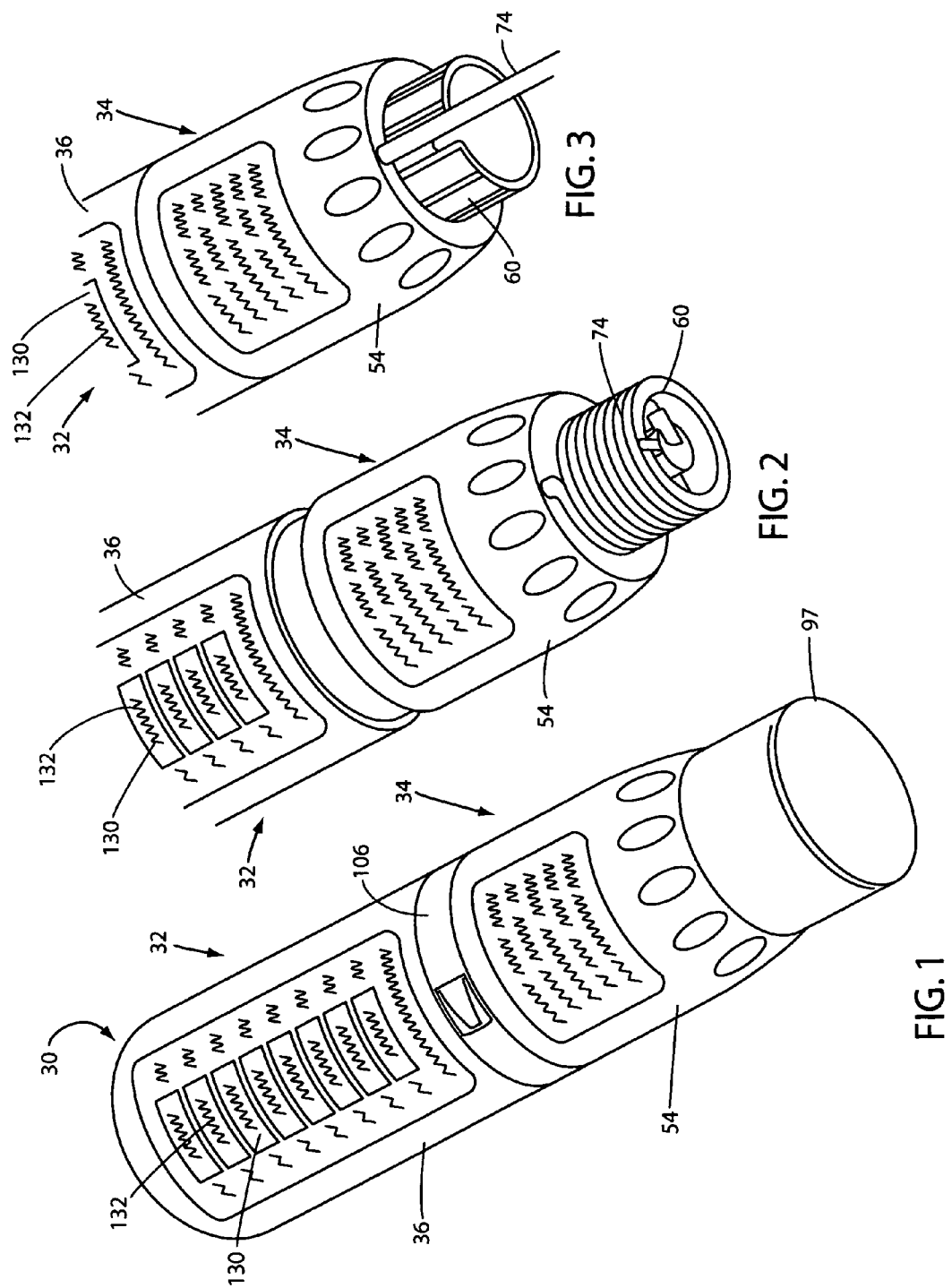

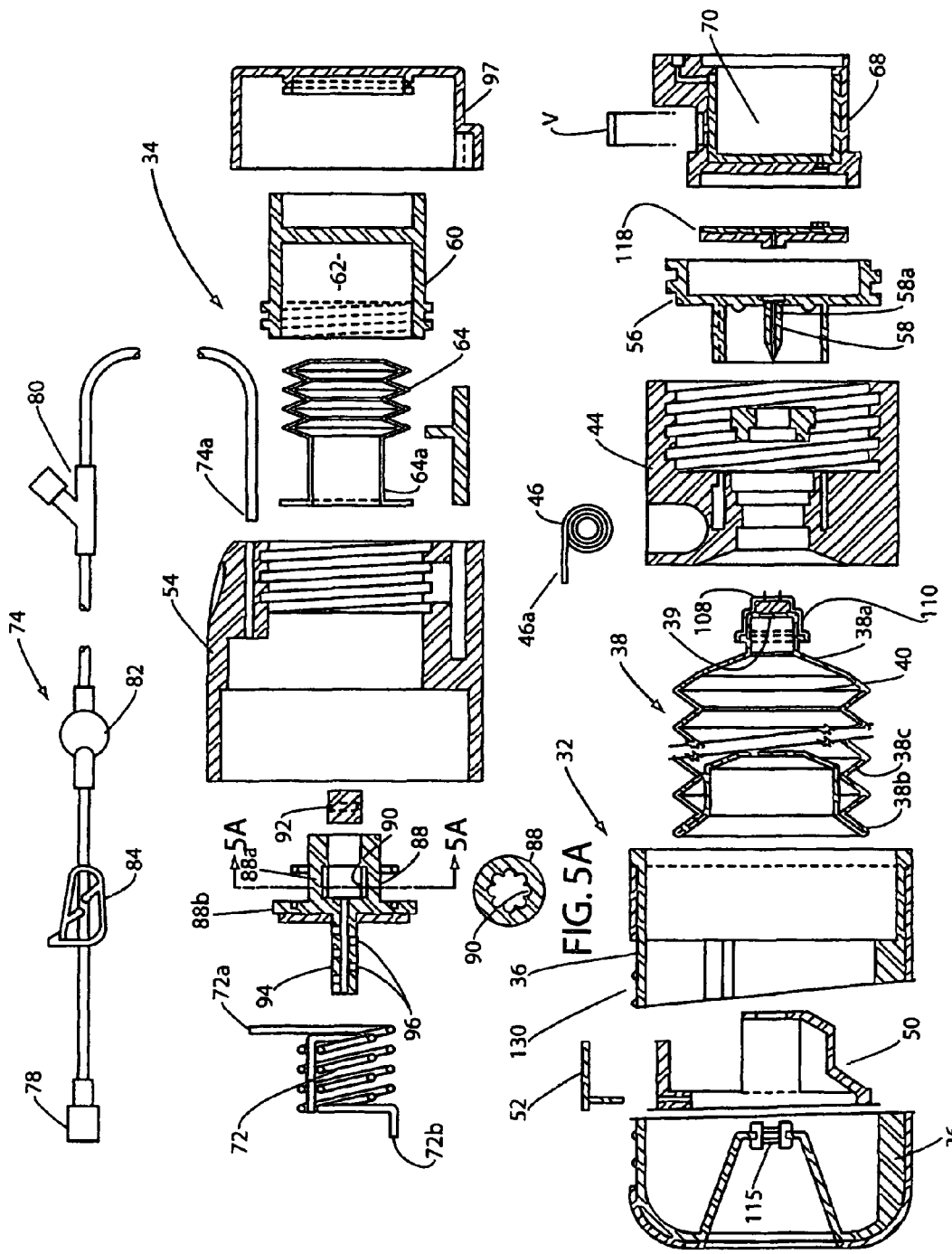

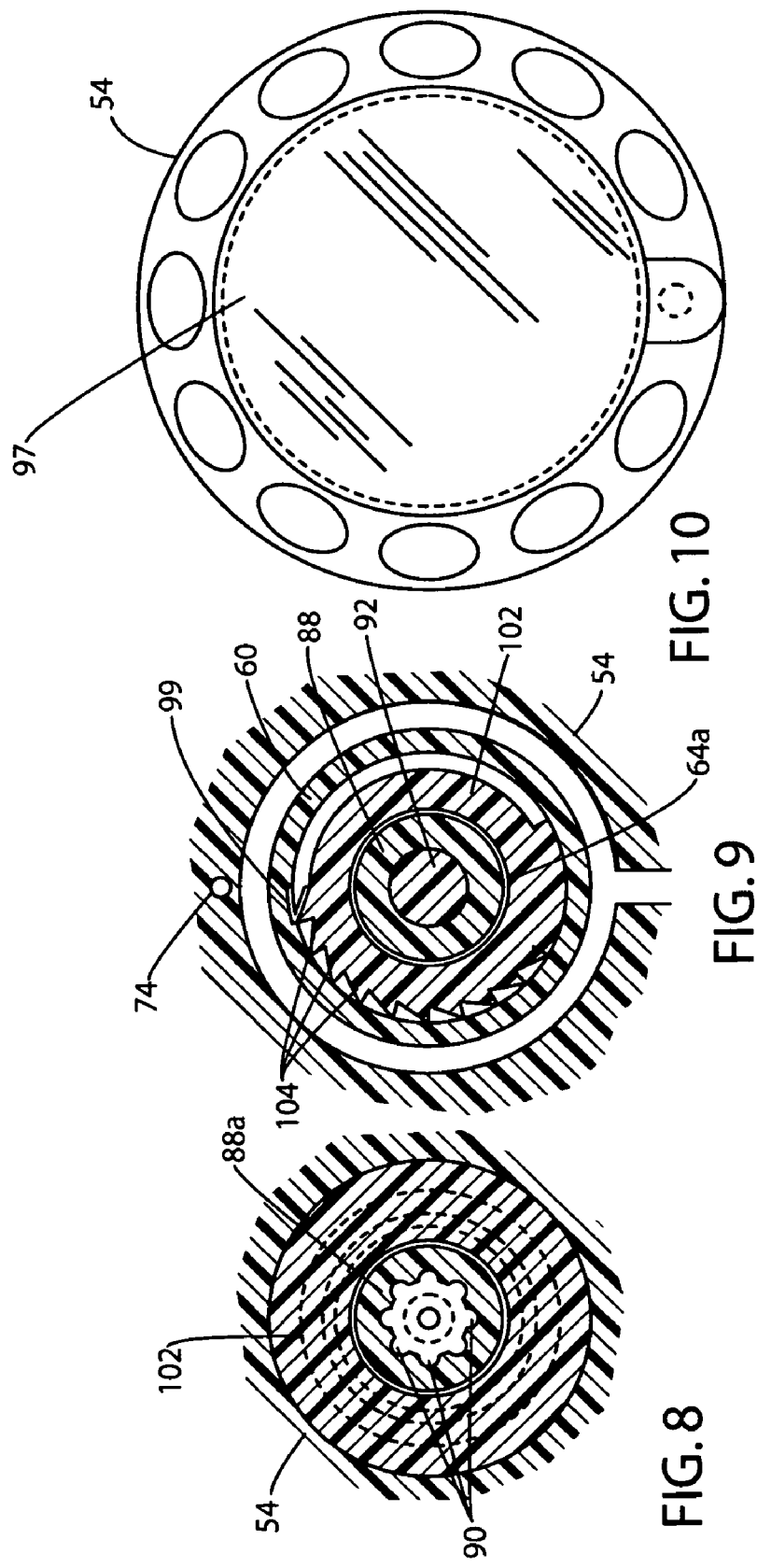

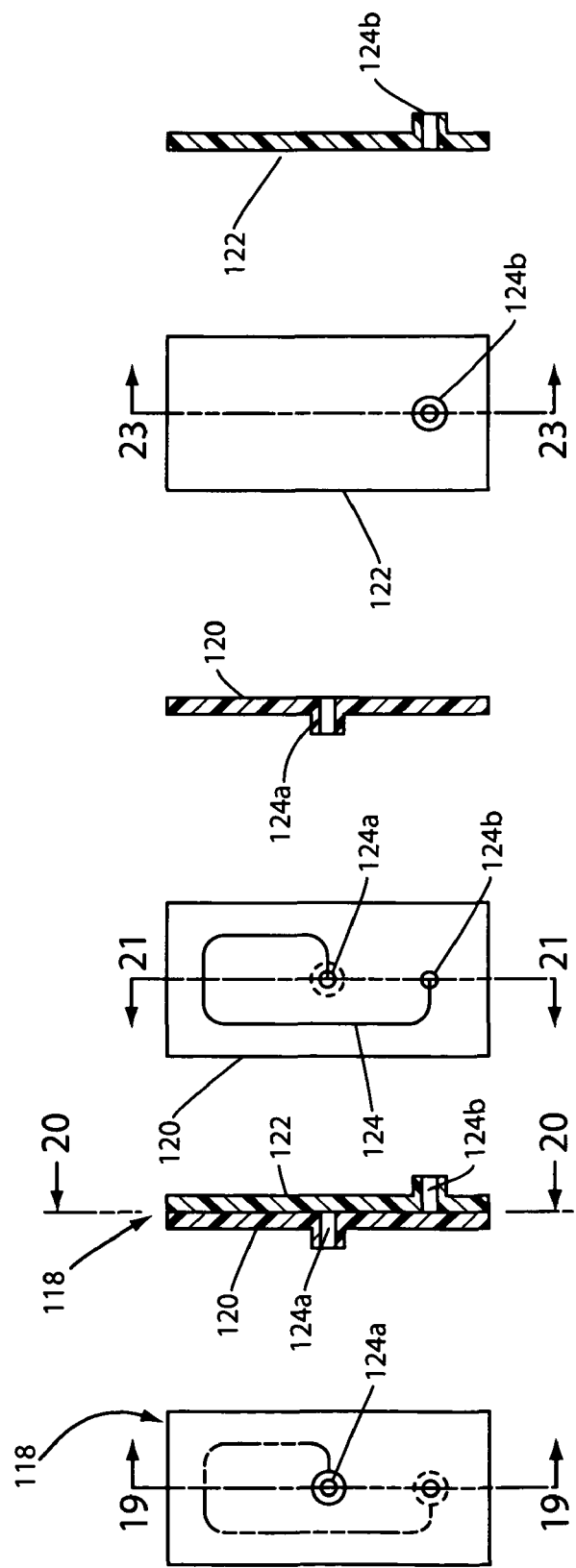

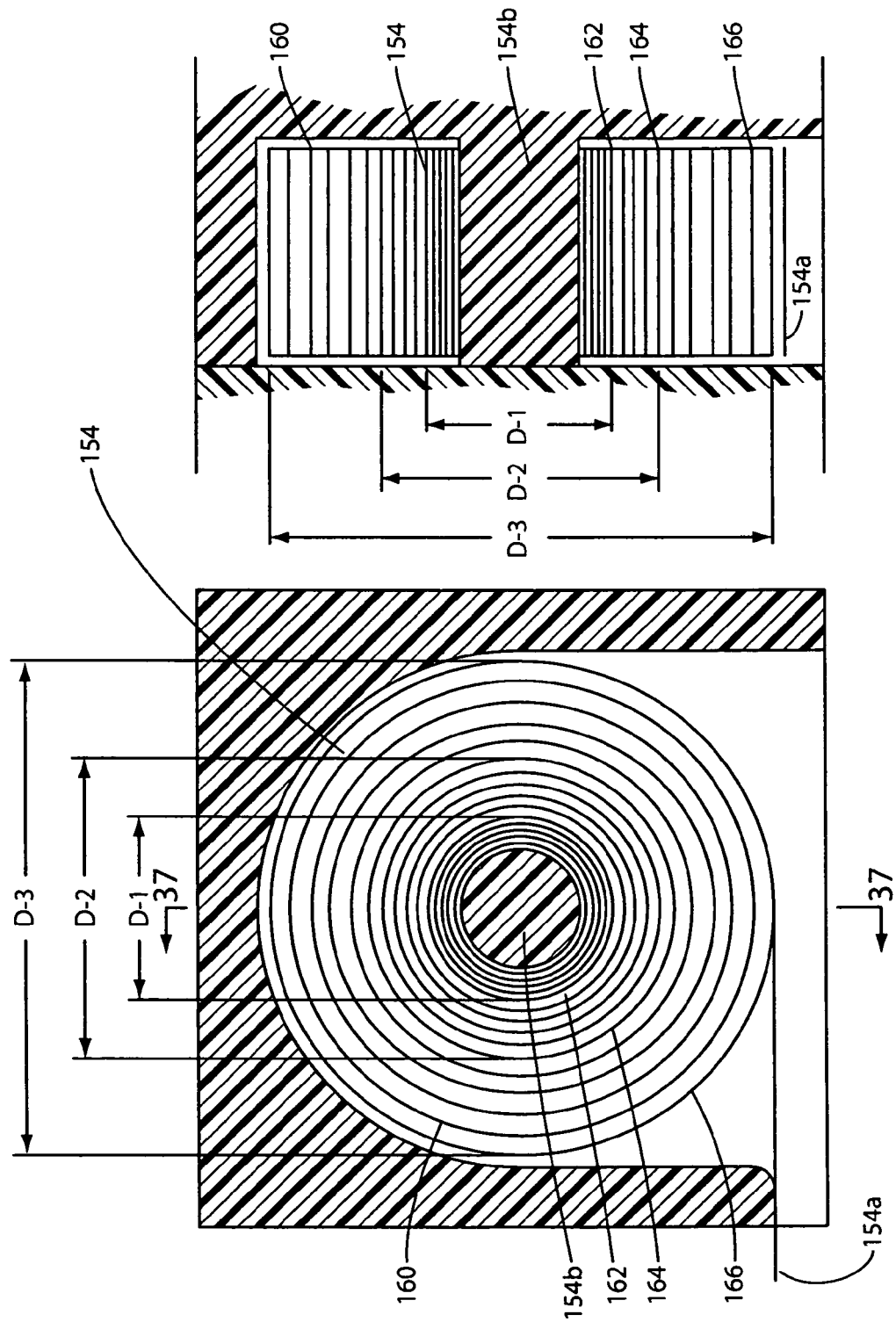

FLUID DISPENSER WITH NON-ELECTRIC FLUID HEATING COMPONENT

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to fluid dispensing devices. More particularly, the invention concerns a novel medicament dispenser for dispensing medicinal fluids, such as plasma expanders of the character used to replace traditional blood based products, to ambulatory patients that uniquely comprise a fluid warming or cooling component that selectively either heats or cools the fluid being dispensed by non-electric means.

2. Description of Related Art Including Information Disclosed Under 37 CFR 1.97 and 1.98

Many people die annually from hemorrhages. Treatment for severe hemorrhage usually requires the immediate and rapid infusion of critical fluids to prevent shock by replacing lost blood volume. To conduct this fluid resuscitation efficaciously in an austere environment, the medical professional must be able to easily transport the delivery system and fluid, and then initiate its use under significant logistical constraints. Furthermore, multi-step and time consuming methods for beginning fluid resuscitation can reduce a medical professional's ability to save lives in triage situations where a large number of patients are injured and in need of immediate medical attention.

In order to maximize the chance of survival, fluid resuscitation is often necessary where the casualty must replace the blood volume lost from the wound. Similarly, the use of IV fluids to restore intravascular volume is considered the best way to manage a severe burn casualty and replenish fluids lost in the first 24 hours. Furthermore, fluid warming is often needed to prevent the onset of hypothermia in trauma patients suffering from catastrophic hemorrhage, where military studies suggest the practice of warming IV fluids prior to administration has significantly decreased the rate of preventable deaths. Accidental or uncontrolled hypothermia is also a well-recognized problem among trauma patients, requiring immediate clinical intervention. Moreover, up to 60% of patients admitted to regional trauma centers can be hypothermic.

Although electronic portable fluid warming devices are currently available, they are not optimal for austere environments where weight and cube are of great concern. Current technologies typically rely on extremely heavy and bulky proprietary batteries, or electricity, that the medical professional must carry in addition to IV fluid bags, thereby eliminating space for other necessary medical supplies. Additionally, current technologies are not designed for direct integration to the IV fluid solution or delivery system modality. In other words, in addition to carrying the IV fluid bags, the medic must carry a separate fluid warming device and a separate battery; altogether which occupy more space and weight than the medic can afford. The invention described herein is a chemically driven fluid warming component/apparatus which would integrate in the dispenser or downstream of the dispenser on the administration line, without adding substantial weight or cube to the overall system. Because the technology relies on chemically generated heat, the need for electricity or proprietary batteries is eliminated, making it possible to heat fluids in austere environments where, previously, warming IV fluids was very cumbersome.

Separate to electronic fluid warmers, other fluid warming "sleeves" or "hot packs" exist that can generate enough heat for an IV bag. Contrary to the fluid warming apparatus described herein, however, the sleeves and heat packs require several minutes to an hour to generate enough heat to warm the fluids to the necessary temperature. The length of time it takes to heat fluids with these warmers is insufficient in environments where the rapid delivery of fluids is required to prevent the casualty from hemorrhaging. Therefore, warming sleeves and hot packs also do not serve as ideal solutions in a trauma environment.

By way of additional background, administering intravenous fluids is a complex task that is even more difficult when intravenous volume IV replacement must be accomplished in the field. Very specific guidelines exist regarding appropriate physiological parameters that caregivers should use to identify which casualties actually require intravenous volume IV replacement in the field. Once intravenous or intra-osseous access is obtained and secured, current technology requires the caregiver to assemble the components of the IV solution prior to administration. A drip chamber must be connected to the fluid bag, the connecting line must be flushed, and then the line must be connected to the infusion site. When utilizing an intra-osseous site, the fluid bag then must be used in conjunction with a pressure infusing device to ensure appropriate flow rates. The complex logistical requirements for ordering, obtaining and storing appropriate medical supplies make the current technology most difficult. Further, the complexity of the process significantly jeopardizes safe and effective patient care within this environment.

As previously mentioned, in order to maximize the chance of survival, fluid resuscitation is often necessary where the casualty must replace the blood volume lost from the wound. Similarly, the use of IV fluids to restore intravascular volume is considered the best way to replenish fluids lost in the first 24 hours. In certain instances, fluid cooling, rather than fluid heating is needed to prevent IV fluids from reaching dangerously hot temperatures. Extremely hot IV fluids can cause tissue damage and hemolysis, a condition that is characterized by the breakdown of the red blood cell's membrane. Hot fluids can also be a disadvantage in treating heat-stroke casualties in the desert, or other high temperature environments. For example, the average daily temperatures in Iraq and Afghanistan, for example, can be in excess of 54° C. (130° F.) and temperatures exceeding 52.2° C. (126° F.) have been shown to damage tissue and blood cells. Although fluids can be stored at safe temperatures at higher level echelons of care, the medic in the austere environment (echelon 1) is at the mercy of the ambient temperature of the environment.

Although portable fluid cooling systems are currently available, they are not optimal for austere environments where weight, cube, and time required to cool are of great concern. Current electronic technologies are bulky, complex, and not suitable for austere environments due to weight and cube concerns. Alternatively, non-electric cooling pouches require the time consuming step of placing the IV fluid bag in the cooler and waiting 15 or more minutes; a step that is both time consuming and logistically complex as it requires the medic to carry both the IV fluid bag and the cooling pouch. The length of time it takes to cool fluids with these cooling systems is insufficient in environments where the rapid delivery of fluids is required to prevent the casualty from hemorrhaging.

The invention described herein is a chemically driven fluid cooling component/apparatus which would integrate in the dispenser or downstream of the dispenser on the administration line, without adding substantial weight or cube to the overall system. Because the technology relies on chemically generated cooling, the need for electricity or proprietary batteries is eliminated, making it possible to cool fluids in austere environments, where previously cooling IV fluids was very cumbersome. This invention with IV fluid dispenser and the integrated fluid cooling component as a self-contained unit would have significant logistical benefits over the currently used and disparate flexible solution bag, fluid coolers, and heavy batteries.

In an effort to overcome the drawbacks discussed in the preceding paragraphs, a number of different types of medicament dispensers for dispensing medicaments to ambulatory patients have been suggested. In this regard, one of the most versatile and unique fluid delivery apparatus developed in recent years is that developed by one of the present inventors and described in U.S. Pat. No. 7,220,245. This apparatus comprises a compact fluid dispenser for use in controllably dispensing fluid medicaments, such as antibiotics, oncolylotics, hormones, steroids, blood clotting agents, analgesics, and like medicinal agents from prefilled containers at a uniform rate. The dispenser uniquely includes a stored energy source that is provided in the form of a substantially constant-force, compressible-expandable wave spring that provides the force necessary to continuously and uniformly expel fluid from the device reservoir. The device further includes a fluid flow control assembly that precisely controls the flow of medicament solution to the patient.

The unique apparatus of the present invention for dispensing medicaments to a patient comprises an improvement of the apparatus described in U.S. Pat. No. 7,220,245 in that, among other things, the apparatus includes a novel non-electric means for controllably heating, or alternatively cooling the medicaments to be delivered to the patient. More particularly, the present invention uniquely provides an IV fluid dispenser and an integrated fluid warming, or cooling component as a self-contained unit that has significant logistical benefits over the currently used and disparate flexible solution bag, electronic fluid warmer and heavy batteries.

BRIEF SUMMARY OF THE INVENTION

By way of brief summary, one form of the apparatus of the present invention for dispensing medicaments to a patient comprises reservoir assembly and a non-electric heater means connected to the reservoir assembly for controllably heating the medicaments to be delivered to the patient. The heater assembly includes a fluid delivery member and the reservoir assembly includes a housing, an integrally formed, hermetically sealed collapsible container having a fluid reservoir for containing a medicinal fluid, and novel stored energy means mounted within the housing for controllably collapsing the sealed container to deliver the medicinal fluid to the fluid delivery member. In one form of the invention, the stored energy means uniquely comprises a variable force spring and the non-electric heating means comprises an exothermic solution for controllably heating the fluid delivery member. In another form of the invention, the stored energy means uniquely comprises a variable force spring.

With the forgoing in mind, it is an object of the present invention to provide a novel dispensing system for dispensing medicaments to a patient that includes means for controllably heating fluid medicaments within the dispensing system by converting a chemical component, such as calcium chloride, or the like, into a solution by adding a suitable aqueous solution to create an exothermic process causing an increase in temperature of the mixed solution.

Another object of the invention is to provide a novel dispensing system of the aforementioned character that includes a length of tubing through which the fluid medicaments pass that is disposed within a chamber containing the exothermic solution so that the heat from the exothermic solution will transfer directly to the fluid medicaments as the medicaments pass through the length of tubing.

Another object of the invention is to provide a novel dispensing apparatus of the class described that includes a novel flow rate control means that precisely controls the rate of flow of the heated medicinal fluid toward the patient.

Another object of the invention is to provide a novel dispensing apparatus in which a stored energy source is provided in the form of a constant force spring that provides the force necessary to expel the medicinal fluid from the device reservoir.

Another object of the invention is to provide a novel dispensing apparatus in which a stored energy source is provided in the form of a variable force spring that provides the force necessary to expel the medicinal fluid from the device reservoir.

Another object of the invention is to provide a novel dispensing apparatus in which a stored energy source is provided in the form of an elongated pre-stressed strip of spring material that exhibits a cross-sectional mass that varies along said length. This variation in cross-sectional mass along the length of the spring can be achieved in various ways, as for example, by varying the width of the pre-stressed strip along its length, by providing spaced-apart apertures in the pre-stressed strip along its length, or by otherwise changing the amount of material in a pre-determined way so as to generate the desired stress-strain properties.

Another object of the invention is to provide a dispenser of the character described in the preceding paragraphs in which the stored energy source is provided in the form of a variable force spring that comprises a tightly coiled wound band of pre-hardened, perforated spring steel or stainless steel strip with built-in curvature so that each turn of the strip wraps tightly on its inner neighbor. When the strip is extended (deflected), the inherent stress resists the loading force the same as a common extension spring but at a variable rate.

Another object of the invention is to provide a fluid dispensing apparatus of the character described in the preceding paragraphs that embodies an integrally formed, aseptically filled, unitary semi-rigid collapsible container that includes a fluid reservoir that contains the beneficial agents to be delivered to the patient.

Another object of the invention is to provide a fluid dispensing apparatus of the class described which is compact and lightweight, is easy for ambulatory patients to use and is extremely reliable in operation.

Another object of the invention is to provide a fluid dispensing apparatus that is easy and inexpensive to manufacture in large quantities.

Another form of the apparatus of the present invention for dispensing medicaments to a patient comprises reservoir assembly and a non-electric cooling means connected to the reservoir assembly for controllably cooling the medicaments to be delivered to the patient. The cooling assembly includes a fluid delivery member and the reservoir assembly includes a housing, an integrally formed, hermetically sealed collapsible container having a fluid reservoir for containing a medicinal fluid, and novel stored energy means mounted within the housing for controllably collapsing the sealed container to deliver the medicinal fluid to the fluid delivery member. In one form of the invention, the stored energy means uniquely comprises a variable force spring and the non-electric heating means comprises a novel solution for controllably cooling the fluid delivery member. In another form of the invention, the stored energy means uniquely comprises a variable force spring.

With the forgoing in mind, it is an object of the present invention to provide a novel dispensing system for dispensing medicaments to a patient that includes means for controllably cooling fluid medicaments within the dispensing system through a selected endothermic process, as, for example, the reaction of ammonium salts with water, or the reaction of sodium bicarbonate with water.

Another object of the invention is to provide a novel dispensing system of the aforementioned character that includes a length of tubing through which the fluid medicaments pass that is disposed within a chamber containing the endothermic solution so that the heat from the endothermic solution will transfer directly to the fluid medicaments as the medicaments pass through the length of tubing.

Another object of the invention is to provide a novel dispensing apparatus of the class described that includes a novel flow rate control means that precisely controls the rate of flow of the cooled medicinal fluid toward the patient.

BRIEF DESCRIPTION OF SEVERAL VIEWS OF THE DRAWINGS

FIG. 1 is a generally perspective front view of one form of the fluid dispensing apparatus of the present invention.

FIG. 2 is a generally perspective front view similar to FIG. 1, but showing the appearance of the apparatus with the dispenser cover removed.

FIG. 3 is a generally perspective front view similar to FIG. 2, but showing the appearance of the apparatus with the administration line un-coiled from the forward portion of the apparatus.

FIG. 5A is a cross-sectional view taken along lines 5A-5A of FIG. 5.

FIG. 5 is a longitudinal cross-sectional exploded, view of the fluid dispensing system shown in FIG. 4 of the drawings.

FIG. 8 is a cross-sectional view taken along lines 8-8 of FIG. 4.

FIG. 9 is a cross-sectional view taken along lines 9-9 of FIG. 4.

FIG. 10 is a view taken along lines 10-10 of FIG. 4.

FIG. 18 is a rear view of one form of the rate control assembly of the fluid delivery system that includes a rate control plate and the rate control plate cover.

FIG. 19 is a cross-sectional view taken along lines 19-19 of FIG. 18.

FIG. 20 a rear view of the rate control plate of the rate control assembly shown in FIG. 18.

FIG. 21 is a cross-sectional view taken along lines 21-21 of FIG. 20.

FIG. 22 is a front view of the rate control cover of the rate control assembly shown in FIG. 18.

FIG. 23 is a cross-sectional view taken along lines 23-23 of FIG. 22.

FIG. 36 is a greatly enlarged cross-sectional view of one of the springs and spring drums shown in FIG. 35.

FIG. 37 is a cross-sectional view taken along lines 37-37 of FIG. 36.

DETAILED DESCRIPTION OF THE INVENTION

Figure 4:
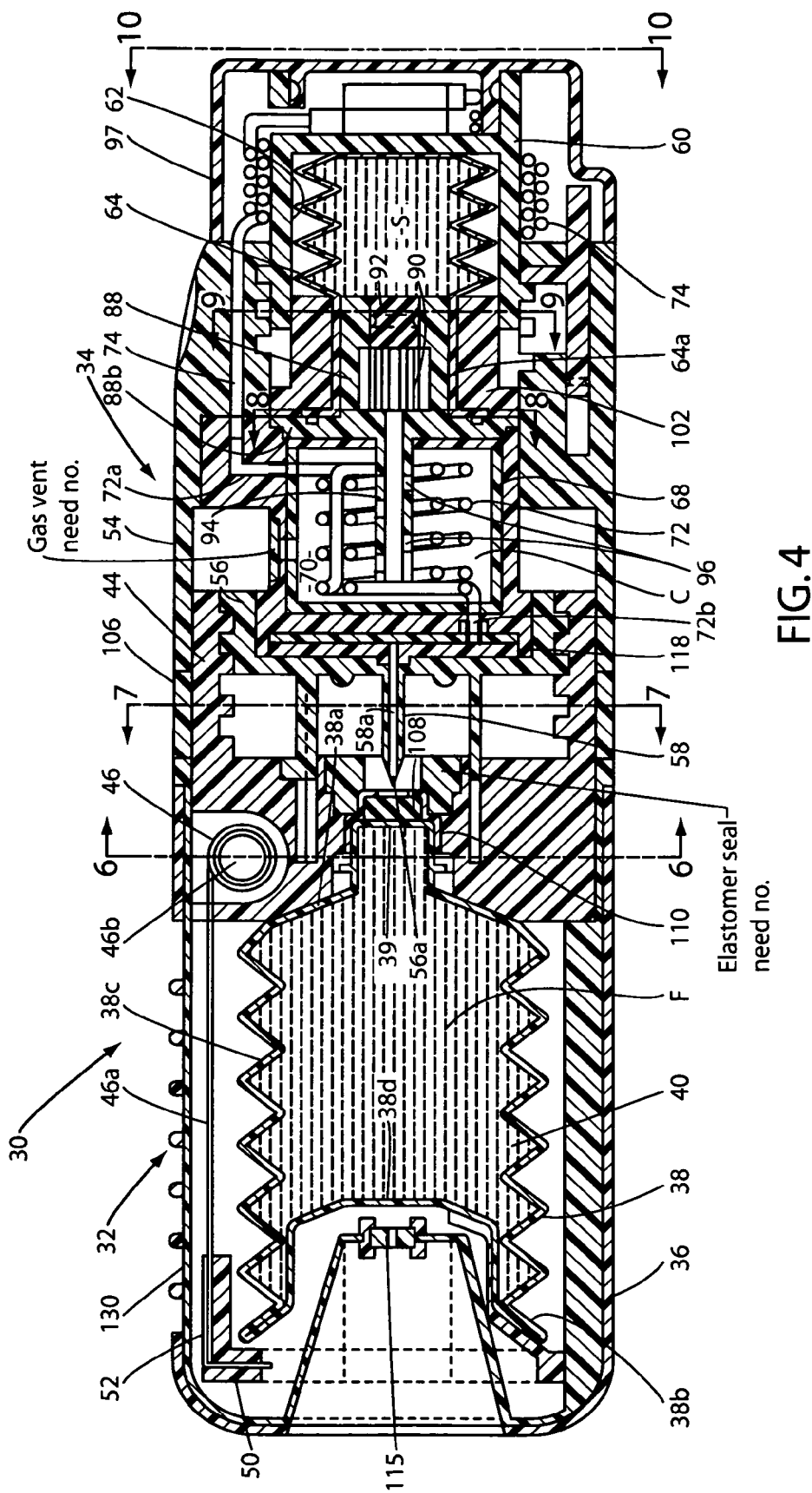
FIG. 4 is a longitudinal cross-sectional view of the fluid dispensing system shown in FIG. 1 of the drawings.
Figure 7:
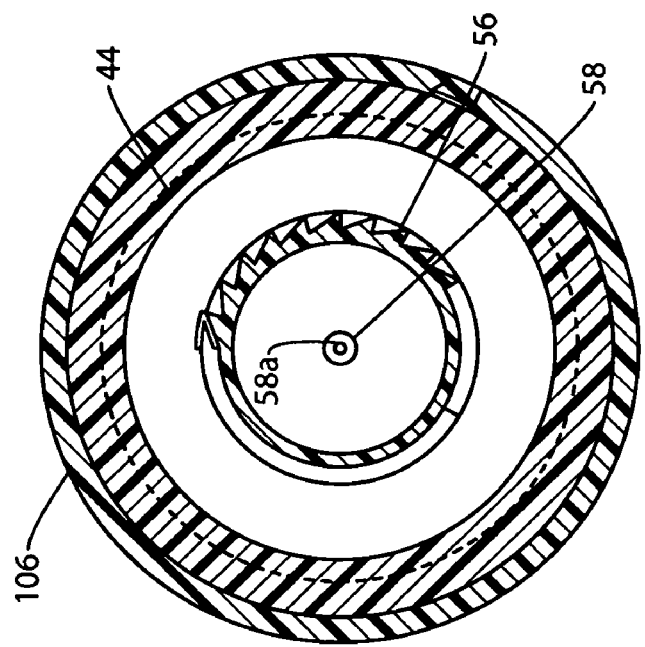
FIG. 7 is a cross-sectional view taken along lines 7-7 of FIG. 4.
Figure 6:
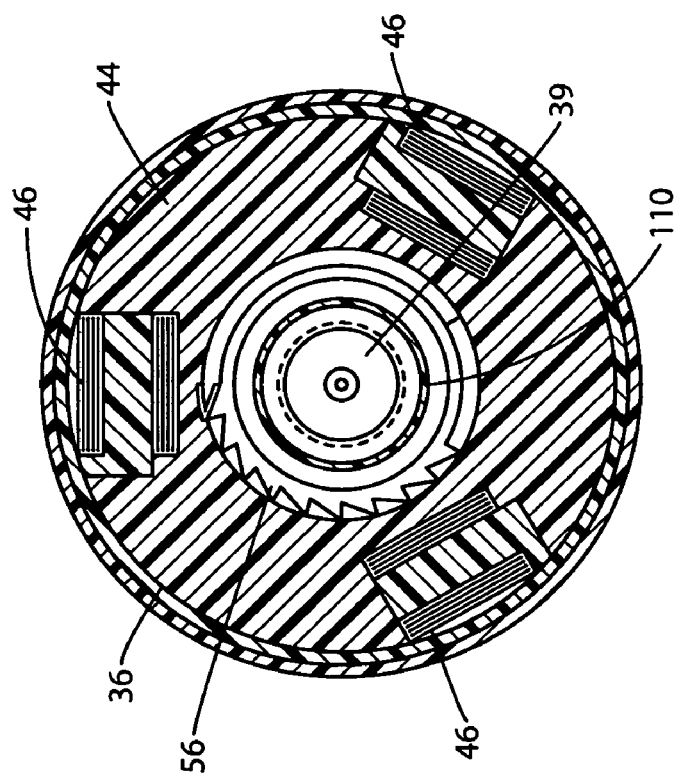
FIG. 6 is a cross-sectional view taken along lines 6-6 of FIG. 4.

Definitions—As used herein the following terms mean:
Unitary Container:
  A closed container formed from a single component.
Continuous/Uninterrupted Wall:
  A wall having no break in uniformity or continuity.
Hermetically Sealed Container:
  A container that is designed and intended to be secure against the entry of microorganisms and to maintain the safety and quality of its contents after pressurizing.
Aseptic Processing:
  The term 'aseptic processing' as it is applied in the pharmaceutical industry refers to the assembly of sterilized components and product in a specialized clean environment.
Sterile Product:
  A sterile product is one that is free from all living organisms, whether in a vegetative or spore state.
Blow-Fill-Seal Process:
  The concept of aseptic blow-fill-seal (BFS) is that a container is formed, filled, and sealed as a unitary container in a continuous manner without human intervention in a sterile enclosed area inside a machine. The process is multi-stepped; pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.
Integrally Formed:
  An article of one-piece construction, or several parts that are rigidly secured together, and smoothly continuous in form and that any such components making up the part have been then rendered inseparable.
Frangible:
  An article, item or object that is capable of being ruptured or broken, but does not necessarily imply any inherent materials weakness. A material object, under load that demonstrates a mechanical strain rate deformation behavior, leading to disintegration.
Spring:
  A mechanical element that can be deformed by a mechanical force such that the deformation is directly proportional to the force or torque applied to it. An elastic machine component able to deflect under load in a prescribed manner and able to recover its initial shape when unloaded. The combination of force and displacement in a deflected spring is energy which may be stored when moving loads are being arrested:
Collapsible:
  To cause to fold, break down, or fall down or inward or as in bent-over or doubled-up so that one part lies on another.
Collapsible Container:
  A dispensing apparatus in which one or more walls of the container are made of a material which will deform (collapse) when pressure is applied thereto; or a dispensing apparatus having a collapsible or telescoping wall structure.
Constant Force Spring:
  Constant force springs are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force; the same as a common extension spring but at a nearly constant (zero) rate. The constant-force spring is well suited to long extensions with no load build-up. In use, the spring is usually mounted with the ID tightly wrapped on a drum and the free end attached to the loading force. Considerable flexibility is possible with constant-force springs because the load capacity can be multiplied by using two or more strips in tandem, or back-to-back. Constant force springs are available in a wide variety of sizes.
Variable Force Spring:
  The general class of variable force springs are those that provide a varying force at varying lengths of distention. Contrary to standard coil springs that display stress-strain properties in accordance with Hook's Law, variable force springs may have a variety of linear or non-linear relationships between spring displacement and the force provided.

As used herein, variable force spring includes an elongated, pre-stressed strip of spring material that may be metal, a polymer, a plastic, or a composite material with built-in curvature so that, like the conventional constant force spring, each turn of the strip wraps tightly on its inner neighbor. Uniquely, in a variable force spring the elongated pre-stressed strip of spring material exhibits a cross-sectional mass that varies along said length. This variation in cross-sectional mass along the length of the spring can be achieved in various ways, as for example, by varying the width of the pre-stressed strip along its length, by providing spaced-apart apertures in the pre-stressed strip along its length, or by otherwise changing the amount of material in a pre-determined way so as to generate the desired stress-strain properties. Alternatively, the term "variable force spring" also refers to extension type springs where the wound bands can be coiled to predetermined varying degrees of tightness. Accordingly, similar to a variable force spring with varying amounts of material, variable force springs with a variation of coil tightness can produce highly specific and desirable linear and non-linear force-distention curves to meet the requirements of the invention described herein.

Referring to the drawings and particularly to FIGS. 1 through 5, one form of the apparatus of the invention for dispensing medicaments to a patient is there shown and generally designated by the numeral 30. The apparatus of this form of the invention comprises reservoir assembly 32 and a temperature altering, or heating-cooling assembly 34 that is connected to the reservoir assembly.

In the present form of the invention, the reservoir assembly 32 comprises a reservoir housing 36 and an integrally formed, hermetically sealed collapsible container 38 that is carried within the reservoir assembly in the manner illustrated in FIG. 4 of the drawings. Collapsible container 38, which comprises a hermetically sealed closed container formed from a single component by a blow-fill-seal process, here includes a front portion 38a, including a closure wall 39, a rear portion 38b and a collapsible accordion-like, continuous, uninterrupted side wall 38c that interconnects the front and rear portions in a manner to define a fluid reservoir 40 for containing a medicinal fluid "F".

Connected to reservoir housing 36 is an internally threaded spring housing 44. Mounted within spring housing 44 for controllably collapsing the sealed container 38 to expel the medicinal fluid therefrom is the important stored energy means of the invention. In the present form of the invention the stored energy means comprises a plurality of circumferentially spaced apart constant force spring assemblies 46.

Figure 11:
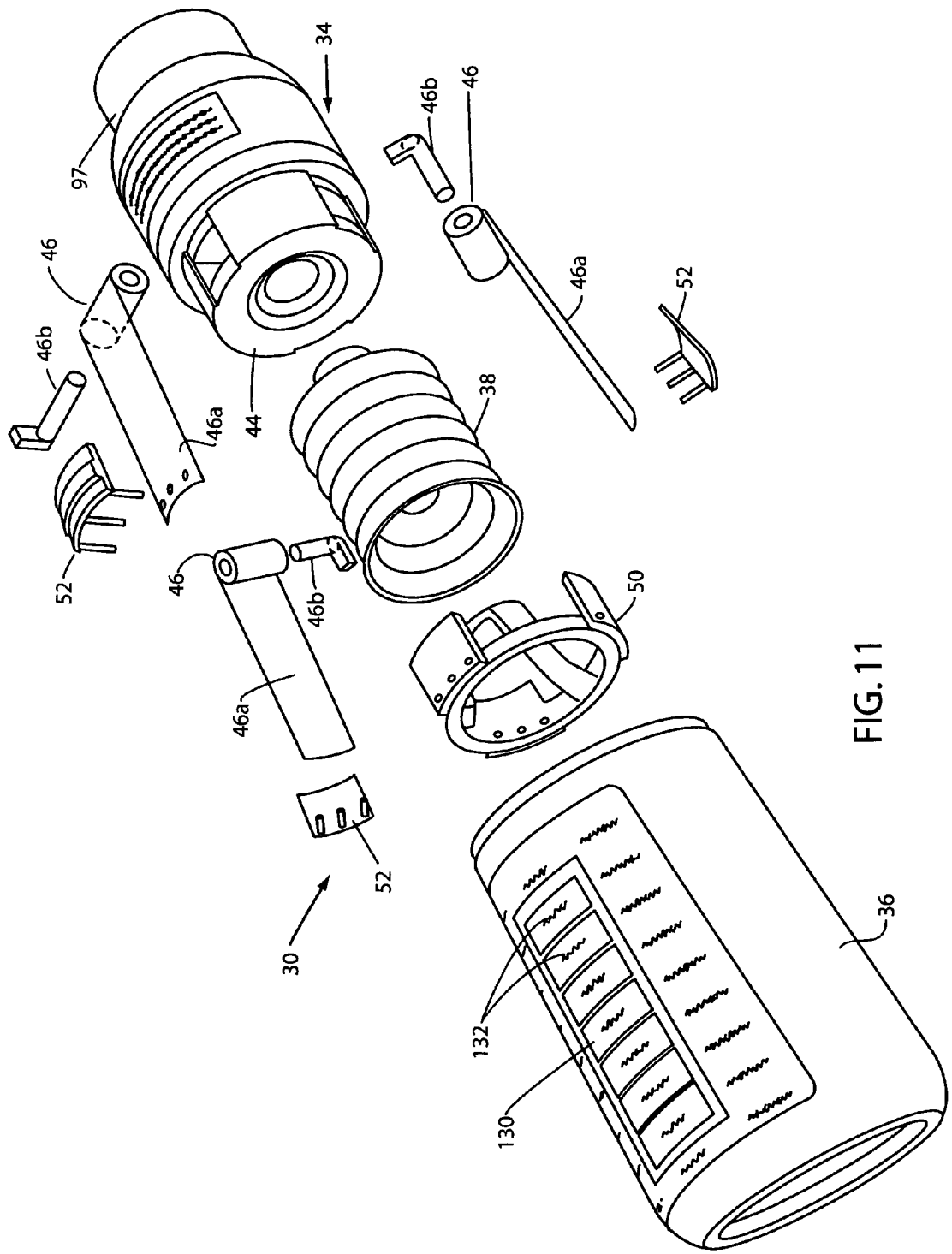
FIG. 11 is a generally perspective, exploded view of the fluid dispensing system shown in FIG. 1 of the drawings.
Figure 12:
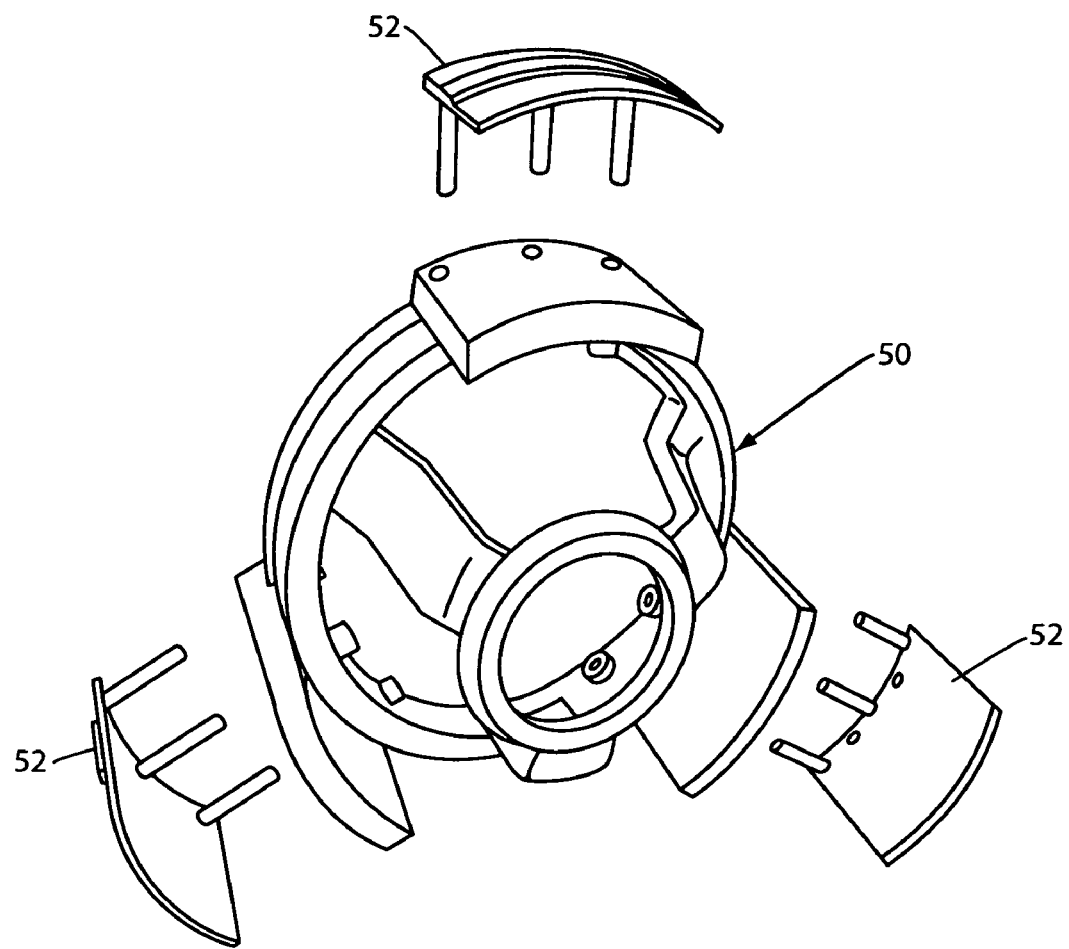
FIG. 12 is a generally perspective, exploded view of the carriage assembly of the fluid dispensing system.

Also forming a part of the reservoir assembly 32 is a carriage 50 that is housed within housing 36 of the reservoir assembly. During the medicament delivery step, carriage 50 is movable by the constant force springs 46 from the first retracted position shown in FIG. 4 of the drawings to the second advanced position shown in FIG. 17 of the drawings. Collapsible container 38 is carried by the carriage 50 (see FIGS. 11 and 12) in the manner best seen in FIG. 4 of the drawings.

The previously identified temperature-altering, or heating-cooling assembly 34 of the apparatus, which is connected to the reservoir assembly 32, here comprises an internally threaded outer shell 54 and an externally threaded reservoir piercing housing 56 that is threadably connected to the spring housing 44 of the reservoir assembly 32 (FIG. 4). Reservoir piercing housing 56 includes a piercing member 58 for piercing the closure wall 39 of the collapsible container 38. As best seen in FIGS. 4 and 5 of the drawings, piercing member 58 is provided with a central fluid passageway 58a.

Threadably connected to internally threaded outer shell 54 for movement between a first retracted position and a second position is an externally threaded control knob 60. Control knob 60 has an interior chamber 62 within which a fluid containing bellows 64 is disposed. For a purpose presently to be described, fluid containing bellows 64 contains a solution or solvent "S" and includes a cylindrically shaped neck portion 64a.

Figure 13:
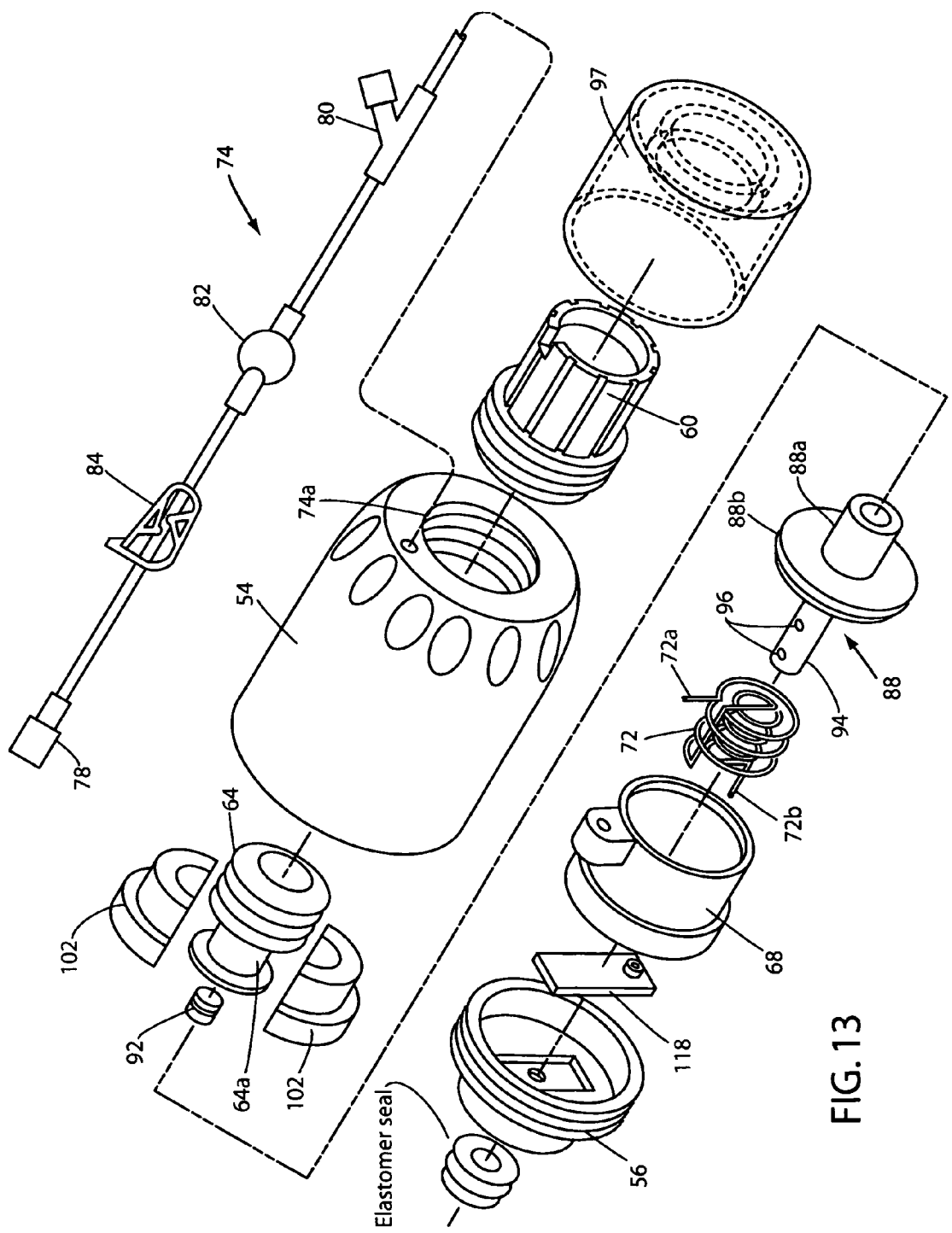
FIG. 13 is a generally perspective, exploded view of the forward portion of the fluid dispensing system.

Forming an important aspect of the temperature altering, or heating-cooling assembly 34 of the apparatus of the invention is a chemical component housing 68 that is carried within outer shell 54 at a location intermediate reservoir piercing housing 56 and the control knob 60. Chemical component housing 68 is provided with an internal chamber 70 that contains a chemical component "C", which upon being mixed with the solution contained within the fluid containing bellows 64 produces either an exothermic process, or alternatively an endothermic process. Disposed within internal chamber 70 of housing 68 is the important fluid delivery member of the apparatus. In the present form of the invention the fluid delivery member is provided of a helix tube 72. As seen in FIGS. 4, 5 and 13 of the drawings, an administration line 74 is connected to end 72a of the helix tube 72, while end 72b of the helix tube is in communication with passageway 58a of the piercing member via the rate control means of the invention. In a manner presently to be described, the important rate control means functions to control the rate of fluid flow from the reservoir 40 of the collapsible container 38 to the patient.

As illustrated in FIGS. 5 and 13 of the drawings, administration line 74 comprises a first end 74a that is connected to end 72a of the helix tube 72 and a second end that is connected to a conventional Luer connector 78. Connected intermediate the first and second ends of the administration line is a conventional injector Y site 80, a conventional gas vent 82 and a conventional line clamp 84.

Disposed within a cylindrically shaped neck portion 64a of a fluid containing bellows 64 is seal plug housing 88 that includes a hollow body portion 88a and a flange portion 88b connected to the hollow body portion. As indicated in FIG. 8 of the drawings, hollow body portion 88a is provided with a plurality of circumferentially spaced bypass flow channels 90 the purpose of which will presently be described. Carried within the hollow body portion of the seal plug housing for movement between a first retracted position and a second position is a seal plug 92. Connected to and extending from the flange portion 88b of the seal plug housing is a dispersion tube 94. As best seen in FIG. 4 of the drawings, the dispersion tube extends into and is disposed in close proximity with the helix tube 72 and is provided a plurality of longitudinally spaced fluid outlet passageways 96 that communicate with the internal chamber 70 of housing 68.

In using the apparatus of the invention, the first step is to remove the cover 97 that is connected to, covers, the forward portion of the apparatus in the manner shown in FIGS. 1 and 4 of the drawings. This done, the administration line 74 is unwound from the control knob 60 and extended outwardly and the manner shown in FIG. 5. The control knob 60 can then be irreversibly threadably advanced relative to the internally threaded outer shell 54 to the position shown in FIG. 17 of the drawings. Referring to FIG. 9 it can be seen that the periphery of control knob 60 is provided with a stop shoulder 99 and a bellows retainer 102 that is disposed within the control knob 60 and is provided with a plurality of circumferentially spaced, yieldably deformable saw tooth like locking tabs 104. Locking tabs 104 function to permit advancement of the control knob to the position shown in FIG. 17 of the drawings, but are configured to engage shoulder 99 in the manner to prevent counter rotation of the control knob.

Figure 17:
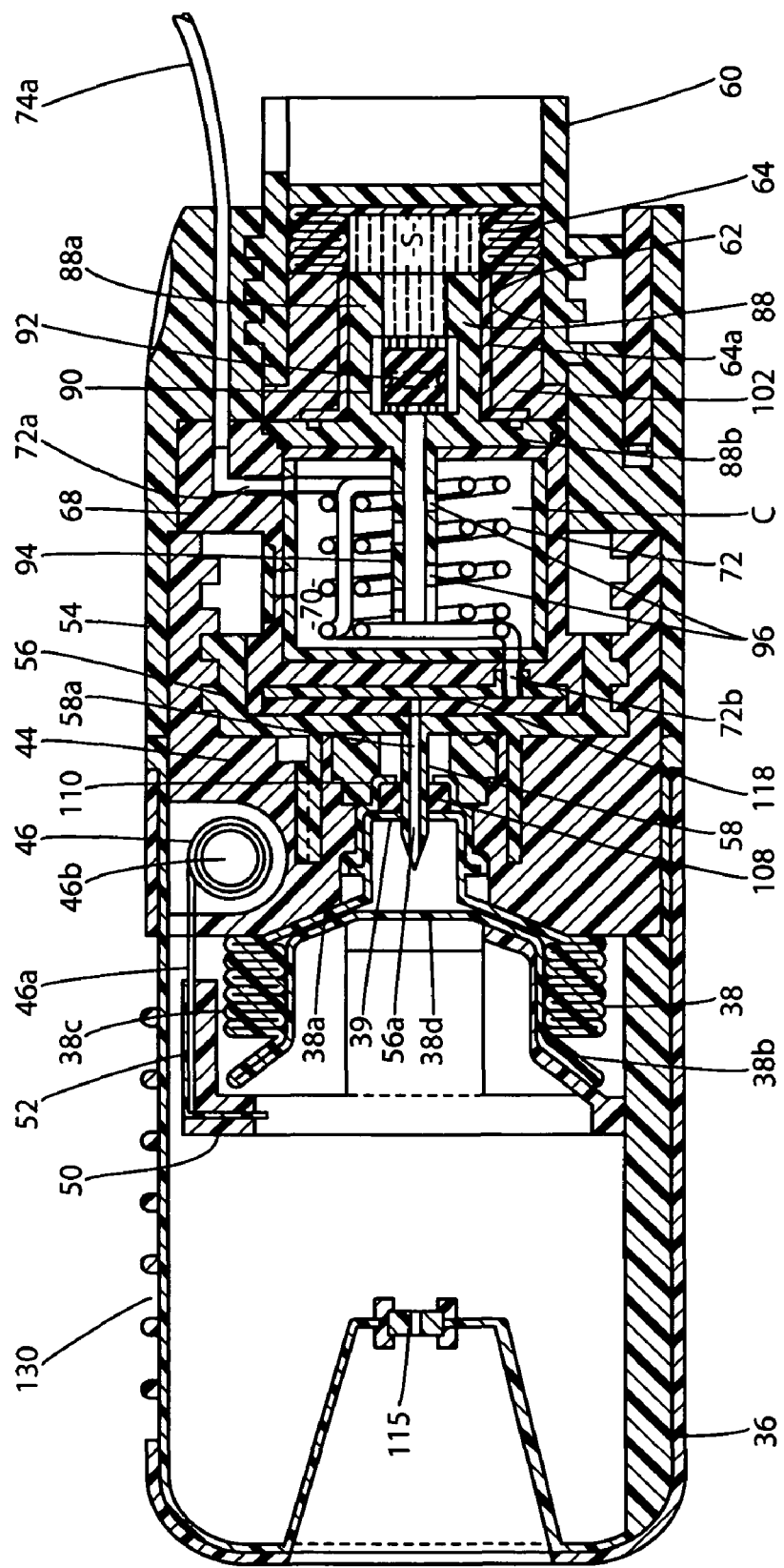
FIG. 17 is a cross-sectional view similar to FIG. 4, illustrating the appearance of the fluid dispensing system following the delivery to the patient of the medicinal fluid contained within a collapsible container of the system.
Figure 24:
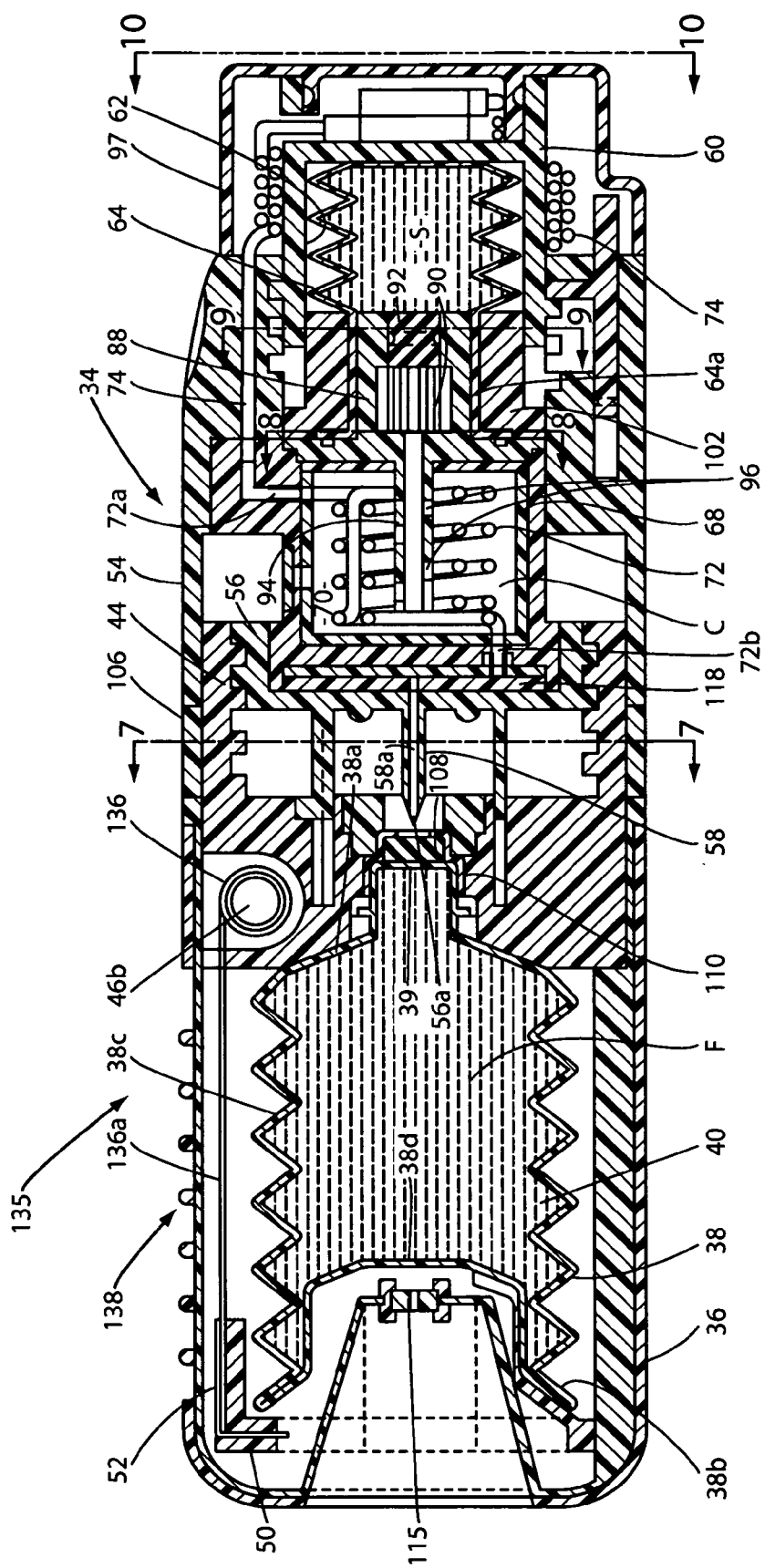
FIG. 24 is a longitudinal, cross-sectional view of an alternate form of the fluid dispensing apparatus of the present invention.

As the control knob is advanced to the position shown in FIG. 17, bellows 64 will be collapsed and the solution or solvent "S" contained within the bellows will be forced through the fluid passageways, or grooves 90 formed in the hollow body portion 88a of the seal plug housing 88. From the fluid passageways 90, the fluid will flow into dispersion tube 94 and then into chamber 70 of housing 68 via the plurality of longitudinally spaced fluid outlet passageways 96 that communicate with internal chamber 70. As the solution or solvent "S" enters chamber 70 it will intermix with the chemical component "C" to cause either an endothermic process, or an exothermic process depending upon the nature of the chemical component "C". If the chemical component "C" causes an exothermic process, the intermixed solution will function to alter the temperature of the fluid delivery member by controllably heating the fluid delivery member, or helix tube 72. If, on the other hand, the chemical component "C" causes an endothermic process the intermixed solution will function to alter the temperature of the fluid delivery member by controllably cooling the fluid delivery member, or helix tube 72. In either event, as bellows 64 collapses, the heated, or cooled intermixed solution will force the seal plug 92 forwardly within body portion 88a and into sealing engagement with flange 88b of the seal plug housing 88, thereby preventing reverse flow of the solution toward the now collapsed bellows 64.

Figure 14:
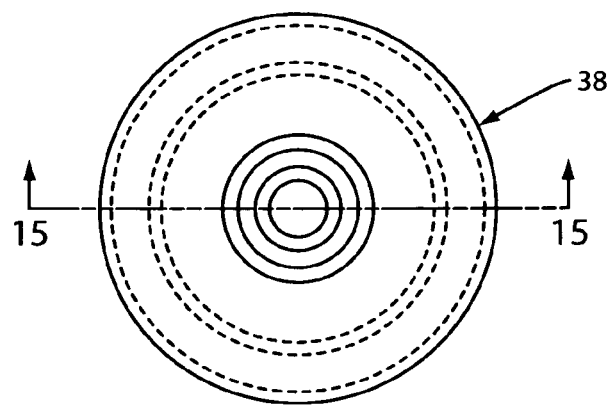
FIG. 14 is an enlarged top plan view of one form of the hermetically sealed collapsible container of the invention.
Figure 16:
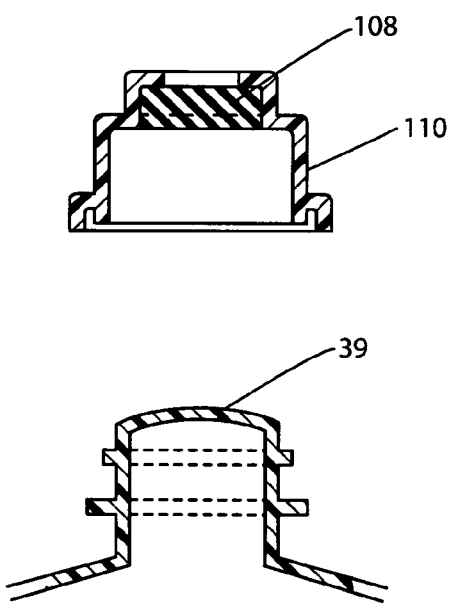
FIG. 16 is an enlarged, fragmentary exploded view of the upper portion of the collapsible container shown in FIG. 15.
Figure 15:
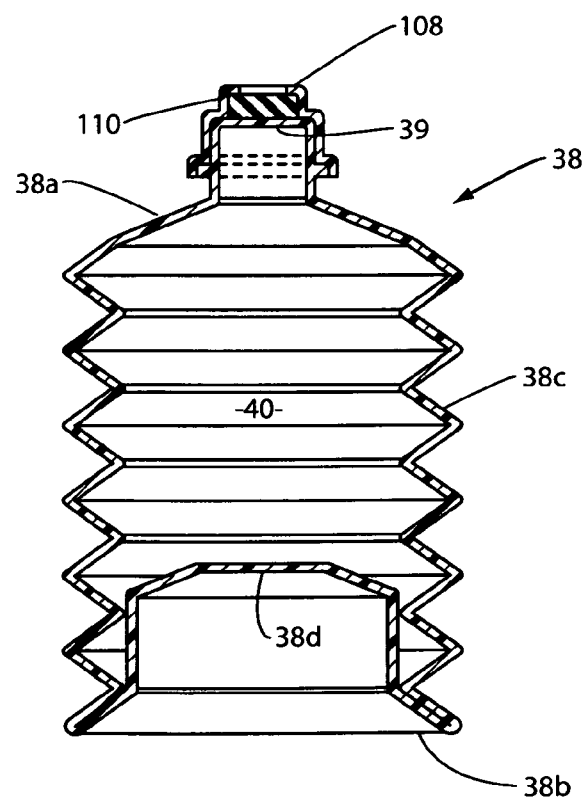
FIG. 15 is a cross-sectional view taken along lines 15-15 of FIG. 14.

The next step in the fluid delivery process is to remove the tear strip 106 that circumscribes spring housing 44 (FIG. 4). Tear strip 106 functions to prevent the relative rotation of the reservoir assembly 32 with respect to the heating assembly 34 and the concomitant advancement of the reservoir piercing housing 56 into the position shown in FIG. 17 of the drawings. In the advanced position shown in FIG. 17, the piercing member 58 pierces the closure wall 39 of the collapsible container 38 as well as an elastomeric septum 108 that is maintained in engagement with the closure wall by a closure cap 110 (see also FIGS. 14, 15 and 16). Movement of the reservoir piercing housing 56 into the position shown in FIG. 17 opens communication between reservoir 40 of the collapsible container 38 and the previously mentioned rate control means of the invention via central passageway 56a of the piercing housing 56.

With communication between the fluid reservoir 40 and the internal fluid passageway 58a of the piercing housing 56 having thusly been established, the fluid contained within the fluid reservoir will be controllably expelled from the reservoir 40 by the action of the stored energy means of the invention, or constant force spring assemblies 46. More particularly, upon penetration of the closure wall 39 of the collapsible container 38, the elongated band portion 46a of the variable force spring assembly will wind about the spring 46 causing the carriage 50, to which portion 46a is interconnected by spring connectors 52 in the manner shown in FIGS. 11 and 12, to move from the first position shown in FIG. 4 to the advanced position shown in FIG. 17. As the carriage moves forwardly, the accordion side walls 38c of the collapsible container 38 will collapse, causing the fluid "F" to be forced outwardly of the reservoir 40 into internal passageway 56a of the piercing housing. As previously mentioned, the fluid will then flow toward the rate control means of the invention which functions to control the rate of flow of fluid from the fluid reservoir 40 toward the patient via the administration set 74 (FIG. 5). During the fluid delivery step, any gases contained within the device reservoir are vented to atmosphere via vent port 115 formed in housing 36.

Referring to FIGS. 4, 5 and 18 through 23, the rate control means of the present form of the invention can be seen to comprise a rate control assembly generally designated by the numeral 118. Rate control assembly 118, which is carried by externally threaded reservoir piercing housing 56, here comprises a rate control plate 120 and a cover 122. Rate control plate 120 is provided with a circuitous micro-channel 124 having an inlet 124a and an outlet 124b. Upon communication between the fluid reservoir 40 and the internal fluid passageway 58a of the piercing member 58 having been established, the fluid contained within the fluid reservoir will be controllably expelled from the reservoir 40 by the action of the stored energy means. The fluid will then flow through the interior passageway 58a of the piercing member 58, into the inlet 124a of the micro channel 124 and then through the micro channel at a controlled rate. The fluid will then flow through the outlet 124b of the micro channel and into the inlet of the helical tube 72. As previously discussed, the fluid within the helical tube will be controllably heated by the exothermic solution contained within internal chamber 70 of housing 68. Finally, the heated fluid will flow from the helical tube and into the administration set for delivery to the patient at a precisely controlled rate depending upon the configuration of the micro-channel 124.

In order that the caregiver can continuously monitor the amount of fluid remaining within the fluid reservoir 40, indicator means are provided for indicating the volume of fluid contained within the reservoir. In the present form of the invention, this indicator means comprises a fluid indicator window 130 provided in the reservoir assembly 32 that enables the caregiver to view the fluid reservoir 40. Indicia 132, which are provided on the fluid indicator window, indicate the volume of fluid contained within the reservoir.

With respect to the exothermic processes previously discussed herein, one of the primary considerations in the choice of a process is the total amount of heat required to warm up the specific volume of fluid and how quickly the fluid needs to reach the required elevated temperature. Several general classes of candidate-exothermic processes which yield a significant amount of heat are as follows:

1. Solvation/dissolution process
2. Acid/base reactions
3. Active metal/water reactions
4. Metal/acid reactions
5. Mixing water and acids
6. Thermite reactions
7. Curing of epoxy resin
8. Setting of cement and concrete Examples of specific reactions in each of the foregoing classes are as follows:

1. Solvation/Dissolution Processes

Anhydrous metal compound+Solvent→Solvated compound or solution $CaCl_{2(s)} + 6H_2O_{(l)} \rightarrow CaCl_2 \cdot 6H_2O_{(s)}$ $\Delta H = -95$ kJ/mol $MgCl_{2(s)} + 6H_2O_{(l)} \rightarrow MgCl_2 \cdot 6H_2O_{(s)}$ $\Delta H = -150$ kJ/mol $FeCl_{3(s)} + 6H_2O_{(l)} \rightarrow FeCl_3 \cdot 6H_2O_{(s)}$ $\Delta H = -121$ kJ/mol $ZnSO_{4(s)} + 7H_2O_{(l)} \rightarrow ZnSO_4 \cdot 7H_2O_{(s)}$ $\Delta H = -108$ kJ/mol $CuSO_{4(s)} + 5H_2O_{(l)} \rightarrow CuSO_4 \cdot 5H_2O_{(s)}$ $\Delta H = -87$ kJ/mol $FeSO_{4(s)} + 7H_2O_{(l)} \rightarrow FeSO_4 \cdot 7H_2O_{(s)}$ $\Delta H = -94$ kJ/mol $Na_2SO_{4(s)} + 10H_2O_{(l)} \rightarrow Na_2SO_4 \cdot 10H_2O_{(s)}$ $\Delta H = -92$ kJ/mol $Ba(OH)_{2(s)} + 8H_2O_{(l)} \rightarrow Ba(OH)_2 \cdot 8H_2O_{(s)}$ $\Delta H = -126$ kJ/mol $BaI_{2(s)} + 7H_2O_{(l)} \rightarrow BaI_2 \cdot 7H_2O_{(s)}$ $\Delta H = -83$ kJ/mol $BaO_{2(s)} + 8H_2O_{(l)} \rightarrow BaO_2 \cdot 8H_2O_{(s)}$ $\Delta H = -96$ kj/mol $Ca(IO_3)_{2(s)} + 6H_2O_{(l)} \rightarrow Ca(IO_3)_2 \cdot 6H_2O_{(s)}$ $\Delta H = -71$ kJ/mol $SrO_{2(s)} + 8H_2O_{(l)} \rightarrow SrO_2 \cdot 8H_2O_{(s)}$ $\Delta H = -117$ kJ/mol 2. Acid Base/Base Reaction Solutions of common acids+Solid base→metal salt+water (HCl, acetic acid, ascorbic acid, oxalic acid, $HNO_3$, $H_3PO_4$, $H_2SO_4$)+(NaOH, KOH, $Mg(OH)_2$, $Ca(OH)_2$, CaO, $Fe_2O_3$, MgO, SrO)

$HCl_{(l)} + NaOH_{(s)} \rightarrow NaCl_{(aq)} + H_2O_{(l)}$ $\Delta H = \mathbf{-332}$ kJ/mol $H_3PO_{4(l)} + SrO_{(s)} \rightarrow Sr_3(PO_4)_{2(s)} + 3H_2O_{(l)}$ $\Delta H = -665$ kJ/mol Solutions of common bases+solid acids $3NaOH_{(aq)} + H_3PO_{4(s)} \rightarrow Na_3PO_{4(aq)} + 3H_2O_{(l)}$ $\Delta H = -322$ kJ/mol 3. Water/Active Metal Reaction $$2K_{(s)}+2H_2O_{(l)} \rightarrow 2KOH_{(aq)}+H_{2(g)} \; \Delta H=-376 \; kJ/mol$$

4. Acid/Metal Reaction $$6HCl_{(aq)}+2Fe_{(s)} \rightarrow 2FeCl_{3(aq)}+3H_{2(g)} \; \Delta H=-856 \; kJ/mol$$

5. Mixing Water and Strong Acids $$H_2SO_{4(l)}+4H_2O_{(l)} \rightarrow H_2SO_4.4H_2O_{(l)} \; \Delta H=-59 \; kJ/mol$$

6. Thermite Reaction $$Metal \; oxide + Al \rightarrow Al_2O_3 + metal$$

$$CuO_{(s)}+Al_{(s)} \rightarrow Al_2O_{3(s)}+Cu_{(s)} \; \Delta H=-1526 \; kJ/mol$$

$$Fe_2O_{3(s)}+Al_{(s)} \rightarrow Al2O3_{(s)}+Fe_{(s)} \; \Delta H=-850 \; kJ/mol$$

7. Curing Epoxy Resin $$Epichlorohydrin+bisphenol\text{-}A \rightarrow polyepoxide$$

8. Curing Cement and Concrete

In any event, the exothermic solution that functions to controllably heat is ideally tailored to heat the fluid to be delivered to the patient to body temperature, or slightly greater than body temperature.

With respect to the endothermic process for cooling the fluid to be delivered to the patient, while the cooling of fluid may, in principle, be achieved through any endothermic process, examples of suitable endothermic chemical processes include the following:

1. Reaction of Ammonium Salts with Water as for Example:

$$NH_4NO_{3(s)}+H_2O_{(l)} \rightarrow HNO_{3(aq)}+NH_{3(aq)}$$

$$NH_4Cl_{(s)}+H_2O_{(l)} \rightarrow HCl_{(aq)}+NH3_{(aq)}$$

$$NH_4IO_{3(s)}+H_2O_{(l)} \rightarrow HIO_{3(aq)}+NH_{3(aq)}$$

2. Reaction of Ammonium Salts with Base as for Example:

$$NH_4Cl_{(s)}+Ba(OH)_2.8H_2O_{(s)}+H_2O_{(l)} \rightarrow BaCl_2.2H_2O_{(aq)}+NH_{3(aq)}+H_2O_{(l)}$$

$$NH_4SCN_{(s)}+Ba(OH)_2.8H_2O_{(s)}+H_2O_{(l)} \rightarrow BaSCN_2.2H_2O_{(aq)}+NH3_{(aq)}+H_2O_{(l)}$$

3. Reaction of Sodium Bicarbonate with Water as for Example:

$$NaHCO_{3(s)}+H_2O_{(l)} \rightarrow NaOH_{(aq)}+CO_{2(g)}$$

4. Reaction of Sodium Carbonate with Acids as for Example:

$$NaHCO_{3(s)}+H_3PO_{4(aq)} \rightarrow Na_3PO_{4(aq)}+CO_{2(g)}$$

$$NaHCO_{3(s)}+CH_3COOH_{(aq)} \rightarrow NaCH_3COO_{(aq)}+CO_{2(g)}$$

$$3NaHCO_{3(s)}+H_3C_6CO_{7(aq)} \rightarrow Na_3C_6CO_{7(aq)}+3CO_2(g)+3H_2O_{(l)}$$

5. Dissolution of Potassium Salts as for Example:

$$KNO_{3(s)}+H_2O_{(l)} \rightarrow KNO_{3(aq)}$$

$$KIO_{3(s)}+H_2O_{(l)} \rightarrow KIO_{3(aq)}$$

$$K_4Fe(CN)_{6(s)}+H_2O_{(l)} \rightarrow K_4Fe(CN)_{6(aq)}$$

6. Evaporation of Innocuous Volatile Solvents as for Example:

$$Water \rightarrow Water \; vapor$$

$$Acetone_{(l)} \rightarrow Acetone_{(g)}$$

$$Pentane_{(l)} \rightarrow Pentane_{(g)}$$

$$Fluorochlorocarbon_{(l)} \rightarrow Fluorochlorocarbon_{(g)}$$

Referring next to FIGS. 24 through 34A of the drawings, an alternate form of the apparatus of the invention for dispensing medicaments to a patient is there shown and generally designated by the numeral 135. This alternate form of dispensing apparatus is similar in many respects to the earlier described embodiments of the invention and like numerals are used in FIGS. 24 through 34A to identify like components. The primary difference between this latest embodiment of the invention and those previously described resides in the provision of a totally different and highly unique stored energy source that is provided in the form of a plurality of variable force spring assemblies 136, the character of which will presently be described. The apparatus of this latest form of the invention comprises reservoir assembly 138 and a heating assembly 34 is connected to the reservoir assembly. Heating assembly 34 is substantially identical in construction and operation to that previously described and reservoir assembly 138 is similar in construction and operation to reservoir assembly 32, save for the differently configured stored energy means.

As before, reservoir assembly 138 comprises a reservoir housing 36 and an integrally formed, hermetically sealed collapsible container 38 that is carried within the reservoir assembly. Connected to reservoir housing 36 is an internally threaded spring housing 44. Mounted within spring housing 44 for controllably collapsing the sealed container 38 to expel the medicinal fluid there from, is the differently configured stored energy means.

Also forming a part of the reservoir assembly 138 is a carriage 50 that is substantially identical in construction and operation to that previously described and to which the springs 136a of the variable force spring assemblies 136 are interconnected. During the medicament delivery step, carriage 50 is movable by the variable force springs 136a from a first retracted position to the second advanced position to collapse the collapsible container.

The heating-cooling assembly 34 of this latest embodiment, which is connected to the reservoir assembly 138, is also substantially identical in construction and operation to that previously described. Similarly, the externally threaded reservoir piercing housing 56 that is threadably connected to the spring housing 44 of the reservoir assembly is substantially identical in construction and operation to that previously described.

Turning now to a more detailed consideration of the novel stored energy source, or variable force spring assemblies 136, which form an extremely important feature of this latest form of the invention. Spring assemblies 136 here comprise a modification of a typical constant force spring assembly, such as a Negator spring "NS". Negator springs, which are of the general character illustrated in FIGS. 25 and 26 of the drawings, are readily commercially available from a number of sources including Stock Drive Products/Sterling Instruments of New Hyde Park, N.Y.

Figure 25:
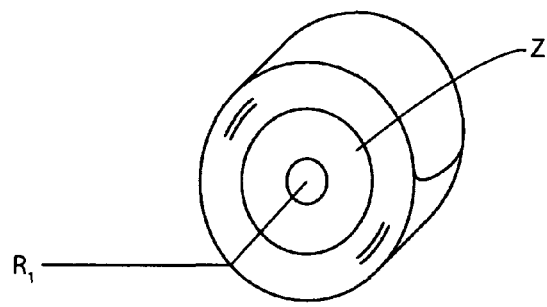
FIG. 25 is a generally perspective view of a prior art retractable spring.
Figure 26:
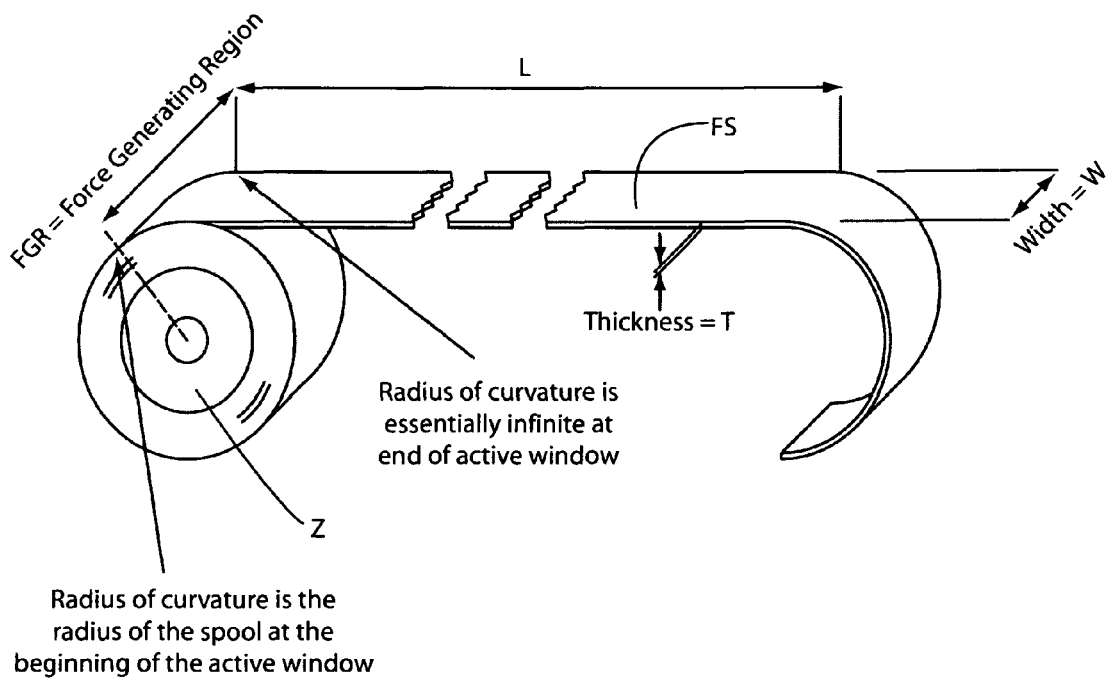
FIG. 26 is a generally perspective view of the prior art retractable spring shown in FIG. 25 as it appears in a partially expanded configuration.

The prior art Negator extension spring assemblies comprises a pre-stressed flat strip "FS" of spring material that is formed into virtually constant radius coils around itself or on a drum "Z" having a radius R-1 (FIG. 25). The area identified in FIG. 26 of the drawings as "FGR" designates the "active region" or "the force generating region" of the constant force spring. It should be understood that in this "active region" the radius of curvature of the spring changes and it is this change in radius of curvature of the spring that is responsible for the generation of the force. In fact, the radius of curvature changes from essentially infinity to a value equal to the radius R-1 of the spool on which the spring is wound. As will be discussed in greater detail hereinafter, increasing the mass of material in this "force generating region" will increase the force provided by the spring. Conversely, decreasing the mass of material in the "force generating region" as is done in springs 136a, will result in a reduction of the force generated by the spring. The mass in the active region can be changed by changing the density of material of the spring as was done in spring 136a, or by changing the thickness of the spring, the width of the spring, or any combination of these. It should be further noted that because the force generating region takes up some portion of the length of the spring it will tend to average any point-by-point changes in physical or structural properties of the spring. The variable L shown in certain of the drawings is defined to be the distance from the force generating region to the end of the spring. When deflected, the spring material straightens as it leaves the drum. This straightened length of spring actually stores the spring's energy through its tendency to assume its natural radius.

The force delivered by a typical prior art constant force spring, such as the Negator extension spring, depends on several structural and geometric factors. Structural factors include material composition and heat treatment. Geometric factors include the thickness of the spring "T", the change in radius of curvature of the spring as the spring is extended, and the width "W" of the spring.

The novel variable force springs of the present invention, including springs 136a, can be constructed from various materials such as metal, plastic, ceramic, composite and alloys, that is, intermetallic phases, intermetallic compounds, solid solution, metal-semi metal solutions including but not limited to Al/Cu, Al/Mn, Al/Si, Al/Mg, Al/Mg/Si, Al/Zn, Pb/Sn/Sb, Sn/Sb/Cu, Al/Sb, Zn/Sb, In/Sb, Sb/Pb, Au/Cu, Ti/Al/Sn, Nb/Zr, Cr/Fe, non-ferrous alloys, Cu/Mn/Ni, Al/Ni/Co, Ni/Cu/Zn, Ni/Cr, Ni/Cu/Mn, Cu/Zn, Ni/Cu/n. These springs comprise a novel modification of the prior art constant force springs to provide variable springs suitable for use in many diverse applications.

As previously discussed, one means of producing the required variable force spring is to make a specific type of modification to a "constant force spring", such as by removing material from the interior of the spring, a slot, or removing material from the edges of the spring, or both.

Figure 27:
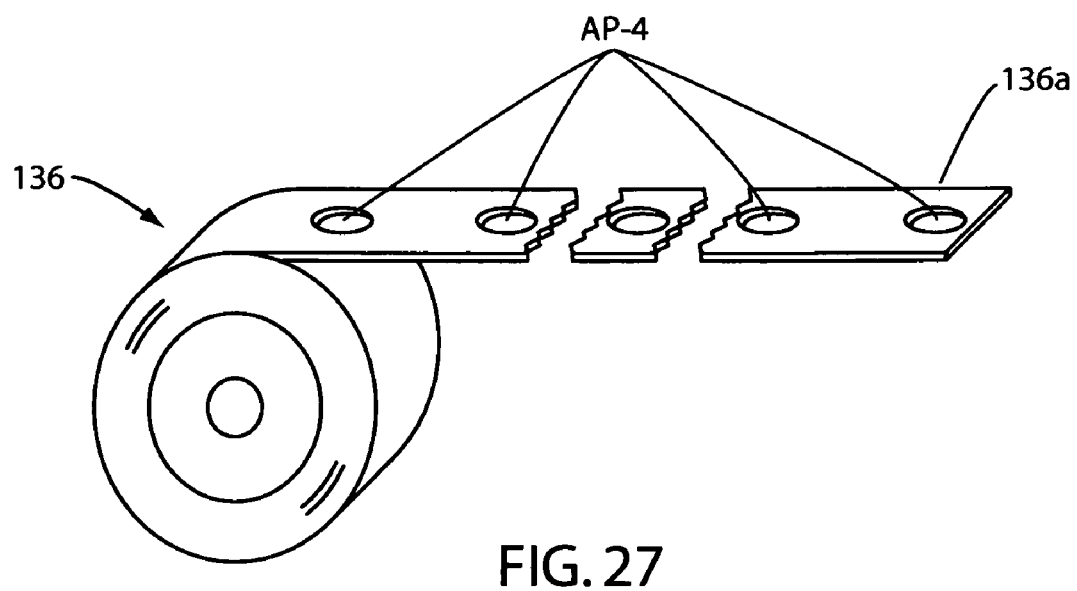
FIG. 27 is an enlarged generally perspective view of the retractable spring shown in FIG. 24.
Figure 27A:
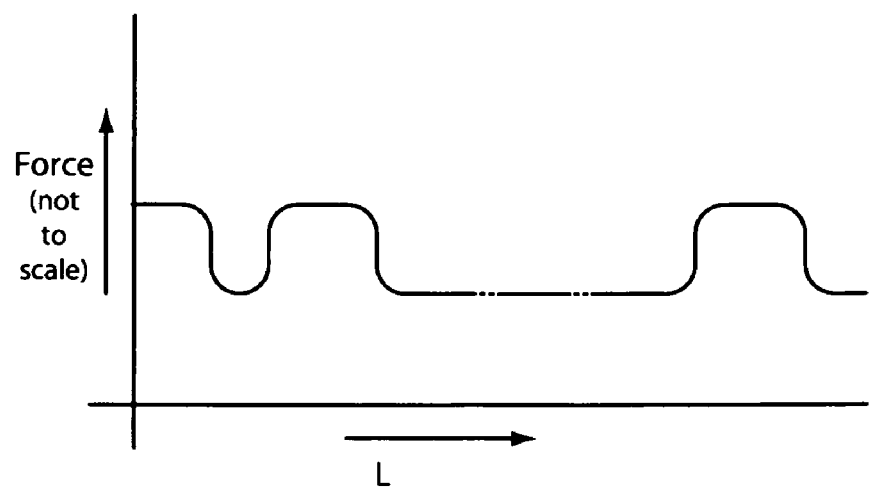
FIG. 27A is a generally graphical representation plotting force exerted by the spring shown in FIG. 27 versus position along the length of the spring.

Considering now in greater detail the construction of the unique variable force spring 136a of this latest form of the invention, as depicted in FIG. 27, the varying cross-sectional mass is here achieved by a constant force spring wherein the force generating region of the spring has been modified to include a plurality of spaced-apart, generally circular shaped apertures "AP-4" along its length. As shown in FIG. 27A, which is a plot of force versus cross-sectional mass, the spring uniquely provides a decrease in force, followed by an increase in force, followed again by a lengthy decrease in force, followed by an increase in force and then followed by another decrease in force.

Figure 28:
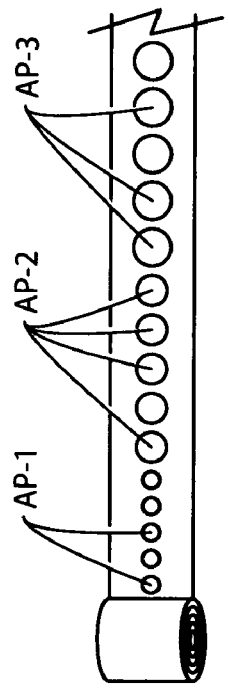
FIG. 28 is a generally illustrative view of the retractable spring of a first modified configuration.
Figure 28A:
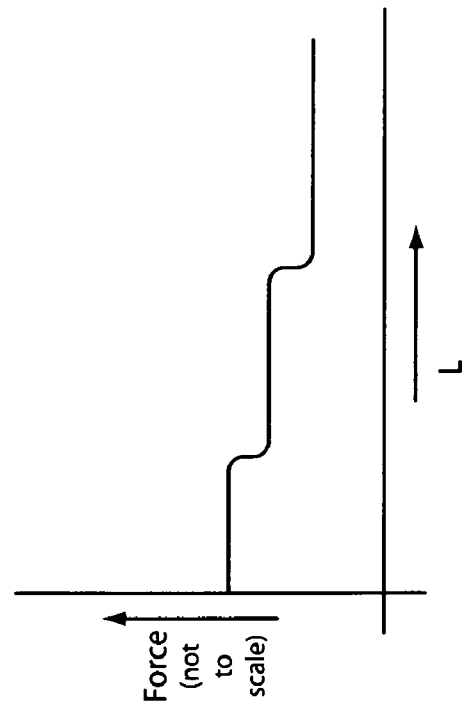
FIG. 28A is a generally graphical representation plotting force exerted by the spring shown in FIG. 28 versus position along the length of the spring.

Referring to FIG. 28, another form of variable force spring having varying cross-sectional mass along its length is there illustrated. In this instance, the varying cross-sectional mass is once again achieved by a constant force spring wherein the force generating region of the spring has been modified to include a plurality of spaced-apart, generally circular shaped apertures of different size, namely "AP-1", "AP-2" and "AP-3" along its length. As shown in FIG. 28A, which is a plot of force versus cross-sectional mass, the spring uniquely provides the desired variable decrease in force followed by the desired variable increase in force as it is retracted.

Figure 29:
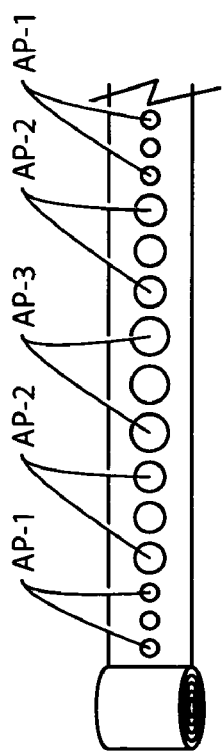
FIG. 29 is a generally illustrative view of the retractable spring of a second modified configuration.
Figure 29A:
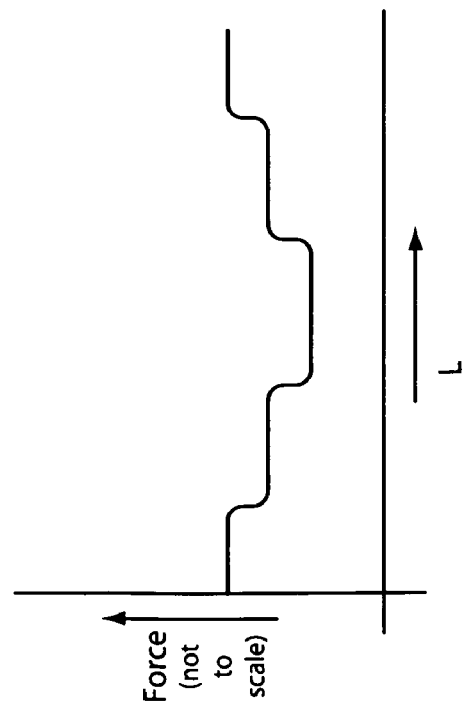
FIG. 29A is a generally graphical representation plotting force exerted by the spring shown in FIG. 29 versus position along the length of the spring.

Turning to FIG. 29, still another form of variable force spring having varying cross-sectional mass along its length is there illustrated. In this instance, the varying cross-sectional mass is once again achieved by a constant force spring wherein the force generating region of the spring has been modified to include a plurality of spaced-apart, generally circular shaped apertures of different size, namely "AP-1", "AP-2", and "AP-3" along its length. As shown in FIG. 29A, which is a plot of force versus cross-sectional mass, the spring uniquely provides the desired variable decrease in force as it is retracted.

Figure 30:
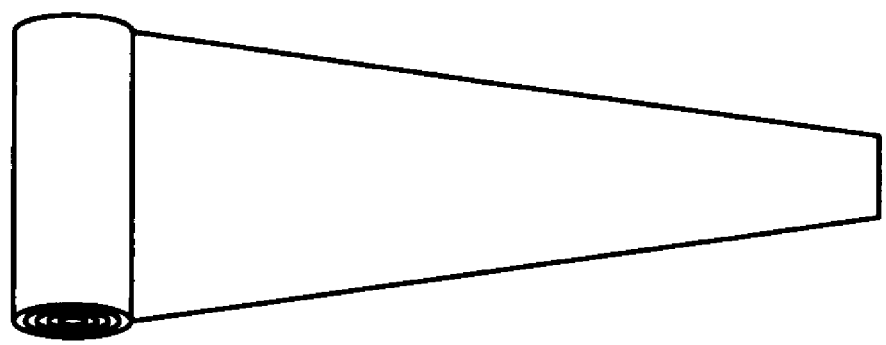
FIG. 30 is a generally illustrative view of the retractable spring of a third modified configuration.
Figure 30A:
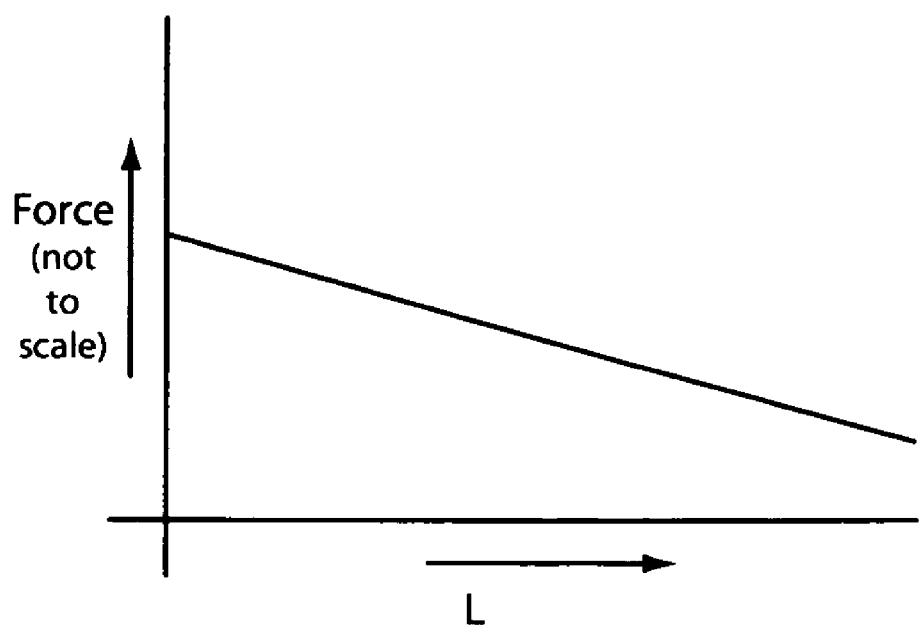
FIG. 30A is a generally graphical representation plotting force exerted by the spring shown in FIG. 30 versus position along the length of the spring.
Figure 31:
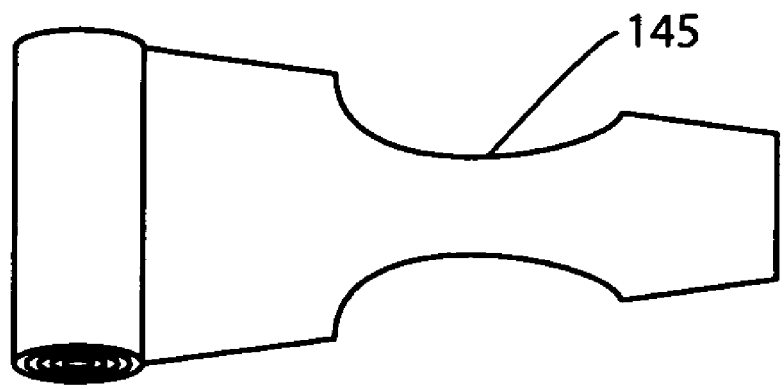
FIG. 31 is a generally illustrative view of the retractable spring of a fourth modified configuration.
Figure 31A:
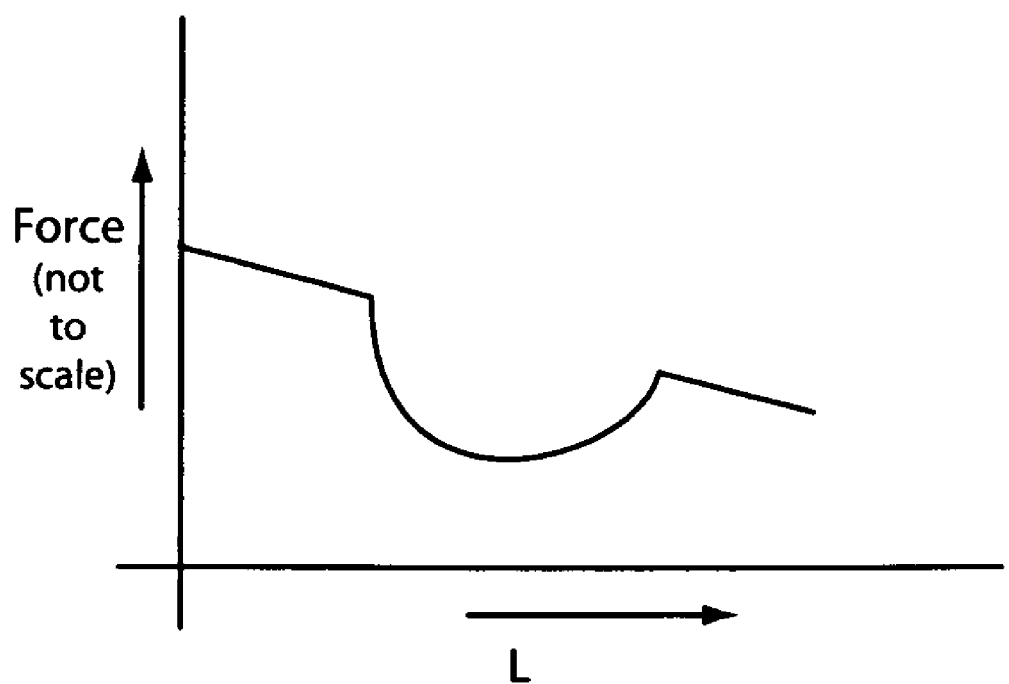
FIG. 31A is a generally graphical representation plotting force exerted by the spring shown in FIG. 31 versus position along the length of the spring.

Referring to FIG. 30 of the drawings, another form of variable force spring having varying cross-sectional mass along its length is there illustrated. In this instance, the varying cross-sectional mass is achieved by a constant force spring that has been modified to exhibit varying width along its length. As shown in FIG. 30A, which is a plot of Force versus "L", where "L" is the distance from the force generating region of the spring to the end of the spring, the spring provides a decreasing force as it is retracted. With regard to the spring depicted in FIG. 31, this spring achieves varying cross-sectional mass by a constant force spring that has been modified to exhibit varying width along its length and also to exhibit at least one area of reduced width along its length. As illustrated in FIG. 31A of the drawings, as this spring rolls up from the extended position shown in FIG. 31, it will provide gradually less force, followed by a non-linear reduction in force at the area designated in FIG. 31 as 145, followed again by a non-linear increase in force, and finally at the point at which it is almost completely retracted, exhibits a gradually decreasing force.

Figure 32:
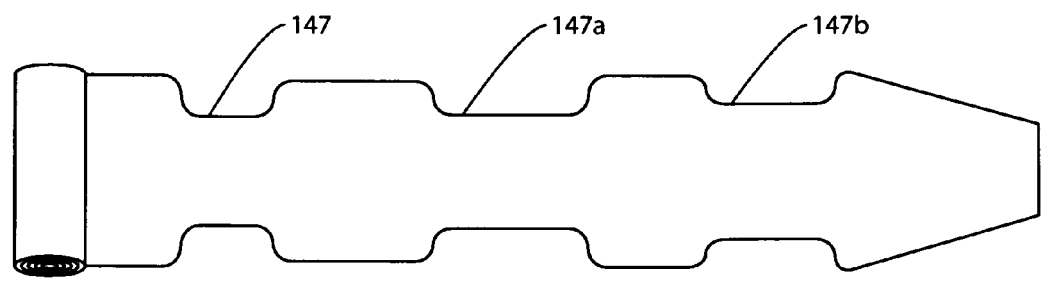
FIG. 32 is a generally illustrative view of the retractable spring of a fifth modified configuration.
Figure 32A:
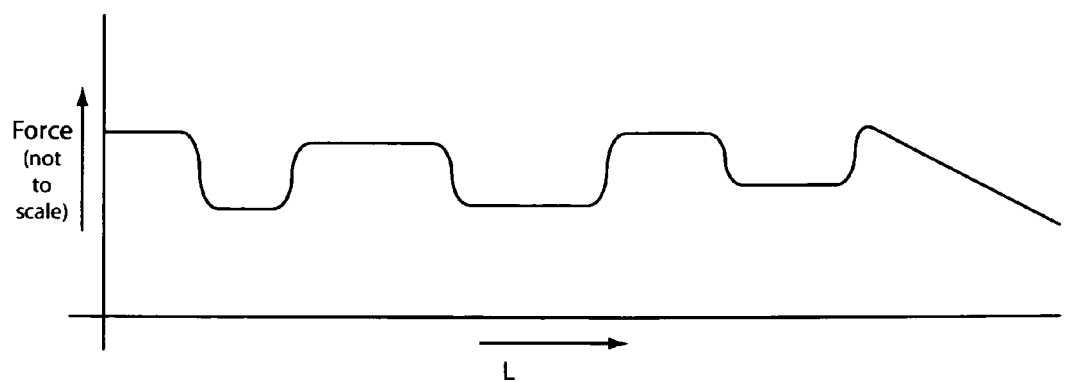
FIG. 32A is a generally graphical representation plotting force exerted by the spring shown in FIG. 32 versus position along the length of the spring.

FIG. 32 is a generally illustrative view of yet another form of retractable spring wherein the varying cross-sectional mass is achieved by a constant force spring that has been modified to exhibit varying width along its length. More particularly, this spring achieves varying cross-sectional mass by a constant force spring that has been modified to exhibit varying width along its length and also to exhibit a plurality of areas of reduced width along its length. As illustrated in FIG. 32A of the drawings, as this spring rolls up from the extended position shown in FIG. 32, it will provide gradually less force, followed by a non-linear reduction in force at the area designated in FIG. 32 as 147, followed again by a non-linear increase in force, followed by a non-linear reduction in force at the area designated in FIG. 32 as 147a, followed by a non-linear decrease in force at the area designated in FIG. 32 as 147b and finally at the point at which it is almost completely retracted, once again exhibits a gradually decreasing force.

Figure 33:
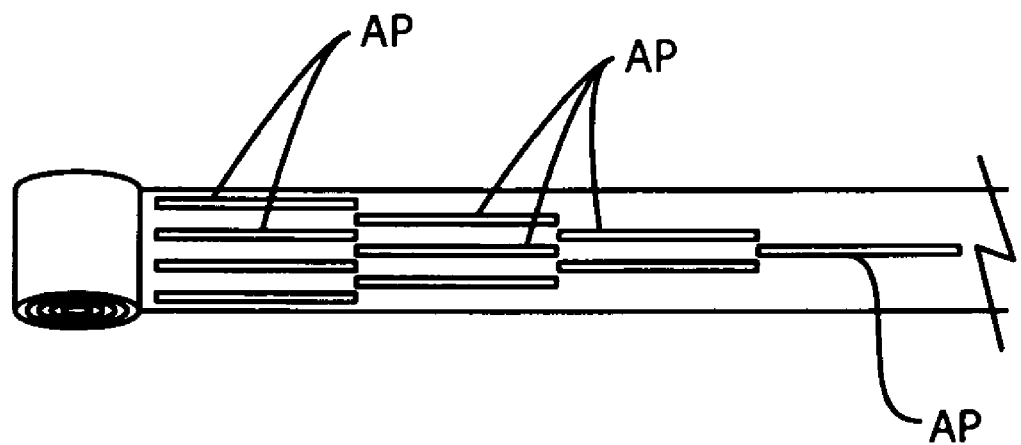
FIG. 33 is a generally illustrative view of the retractable spring of a sixth modified configuration.
Figure 33A:
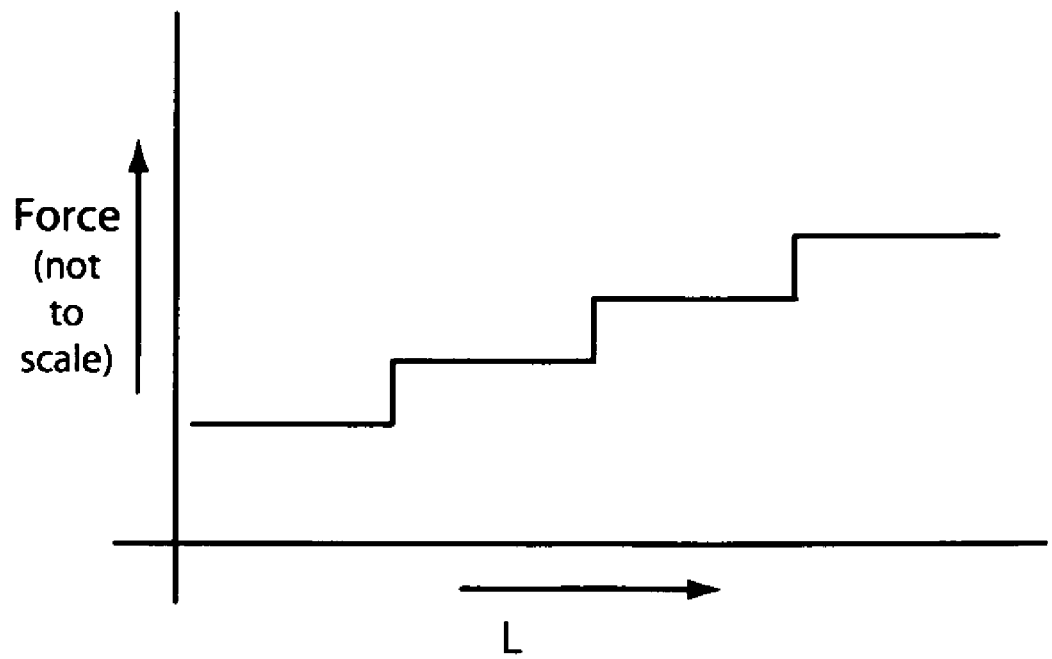
FIG. 33A is a generally graphical representation plotting force exerted by the spring shown in FIG. 33 versus position along the length of the spring.

FIG. 33 is a generally illustrative view of yet another form of retractable spring wherein the varying cross-sectional mass is achieved by a constant force spring that has been modified to exhibit a plurality of the elongated transversely and longitudinally spaced-apart apertures, or slits, AP. As illustrated in FIG. 33A of the drawings, as this spring rolls up from the extended position shown in FIG. 33 it will provide a gradually increasing force in a "stair step" fashion.

Figure 33B:
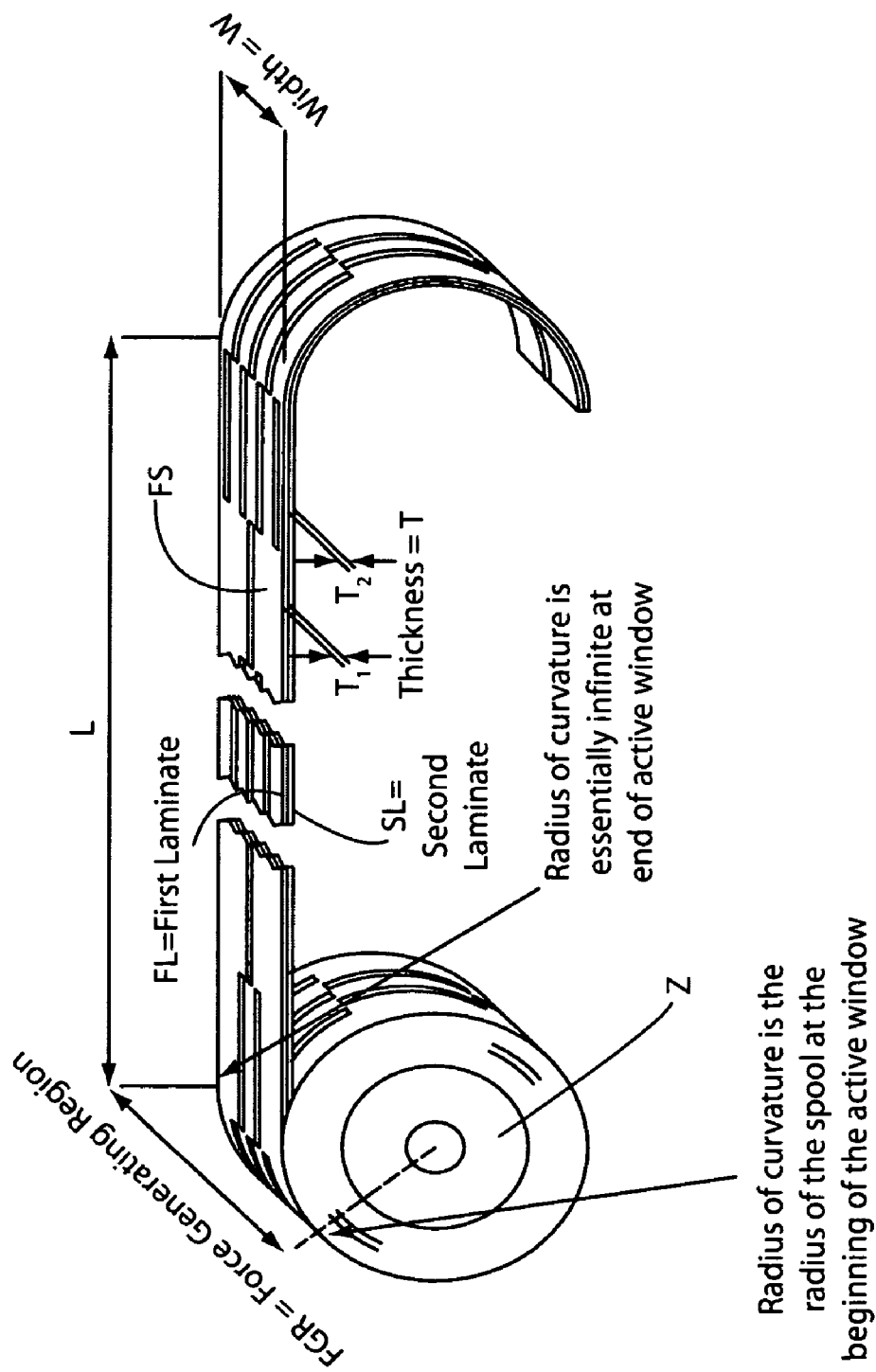
FIG. 33B is a generally perspective view of still another form of modified spring of the invention that here comprises a modification of the sixth modified spring configuration shown in FIG. 33 of the drawings.

FIG. 33B is a generally perspective view of still another form of the retractable spring of a modified configuration that is somewhat similar to that shown in FIG. 33 of the drawings. However, in this latest spring configuration, the spring comprises a novel laminate construction made up of a first laminate FL and a second interconnected laminate SL. The varying cross-sectional mass is once again achieved by providing a plurality of the elongated transversely and longitudinally spaced-apart apertures, or slits.

Figure 34:
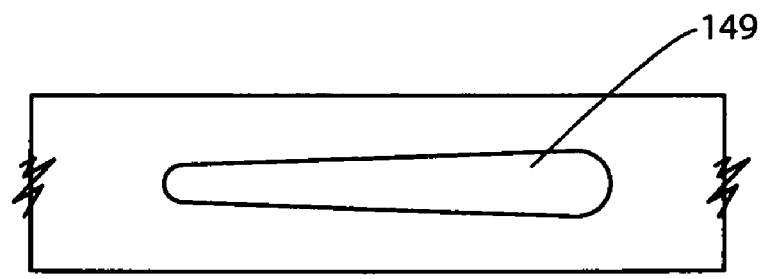
FIG. 34 is a top plan view of the retractable spring of a seventh modified configuration.
Figure 34A:
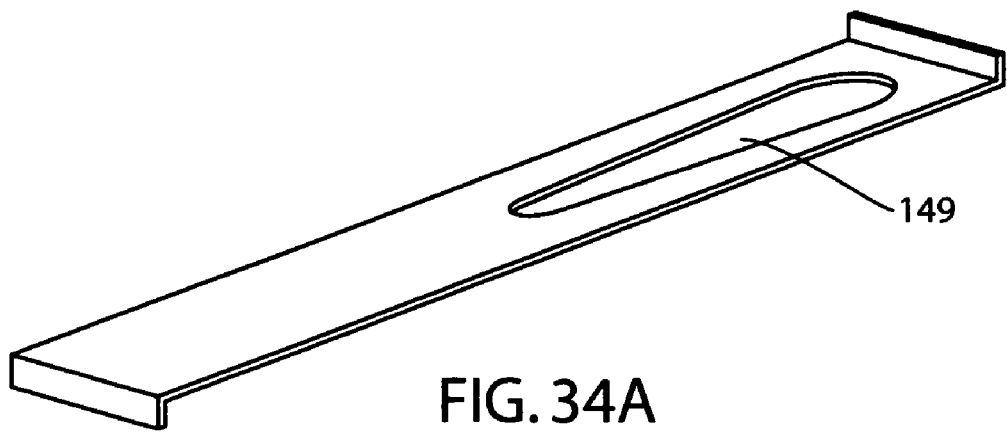
FIG. 34A is a generally perspective view of the retractable spring of the seventh modified configuration.

FIG. 34 is a top plan view of yet another form of retractable spring wherein the varying cross-sectional mass is achieved by a constant force spring that has been modified to exhibit an elongated, generally tear shaped aperture 149 that uniquely varies the force characteristics of the spring by decreasing the mass of material in the "force generating region". This decrease in the mass of material in the "force generating region" by forming the generally tear shaped aperture 149 will result in a predetermined variable force being generated by the spring.

Turning next to FIGS. 35 through 38 of the drawings, still another form of the apparatus of the invention for dispensing medicaments to a patient is there shown and generally designated by the numeral 152. This alternate form of dispensing apparatus is similar in many respects to the earlier described embodiments of the invention and like numerals are used in FIGS. 35 through 38 to identify like components. The primary difference between this latest embodiment of the invention and those previously described resides in the provision of yet another totally different and highly unique stored energy source that is provided in the form of a plurality of variable force spring assemblies 154, the character of which will presently be described. The apparatus of this latest form of the invention comprises reservoir assembly 158 and a heating assembly 34 is connected to the reservoir assembly. Heating assembly 34 is substantially identical in construction and operation to that previously described and reservoir assembly 158 is similar in construction and operation to reservoir assembly 32, save for the differently configured stored energy means.

As before, reservoir assembly 158 comprises a reservoir housing 36 and an integrally formed, hermetically sealed collapsible container 38 that is carried within the reservoir assembly. Connected to reservoir housing 36 is an internally threaded spring housing 44. Mounted within spring housing 44 for controllably collapsing the sealed container 38 to expel the medicinal fluid therefrom is the differently configured stored energy means.

Also forming a part of the reservoir assembly 158 is a carriage 50 that is substantially identical in construction and operation to that previously described and to which the springs 154a of the variable force spring assemblies 154 are interconnected. During the medicament delivery step, carriage 50 is movable by the variable force springs 154a from a first retracted position to the second advanced position to collapse the collapsible container.

The heating assembly 34 of this latest embodiment, which is connected to the reservoir assembly 158, is also substantially identical in construction and operation to that previously described. Similarly, the externally threaded reservoir piercing housing 56 that is threadably connected to the spring housing 44 of the reservoir assembly is substantially identical in construction and operation to that previously described.

Turning now to a more detailed consideration of the novel stored energy source, or variable force spring assemblies 154, which form an extremely important feature of this latest form of the invention. Spring assemblies 154 here comprise the spring 154a in which the elongated band or strip portion 160 of the spring is coiled about the spring drum 154b in predetermined varying degrees of tightness to produce a spring that exhibits a variation of coil tightness that produces highly specific and desirable linear and non-linear force-distention curves to meet the fluid delivery requirements of the apparatus.

Referring particularly to FIGS. 36 and 37 of the drawings, one example of the coiling method is there illustrated. In accordance with this coiling method, the band portion of the spring is initially wound tightly about the drum 154b to produce a first segment 162 having a diameter "D-1". This done, the band portion is then coiled, or wound more loosely about the drum 154b to produce a second segment 164 having a diameter "D-2". Finally, the band portion is coiled, or wound even more loosely about the drum 154b to produce a third segment 166 having a diameter "D-3".

By coiling the springs about their respective drums with a variation of coil tightness in the manner described in the preceding paragraph and as illustrated in FIGS. 36 and 37, springs having highly specific and desirable linear and non-linear force-distention curves can be produced which will meet the fluid delivery requirements of the invention.

Figure 35:
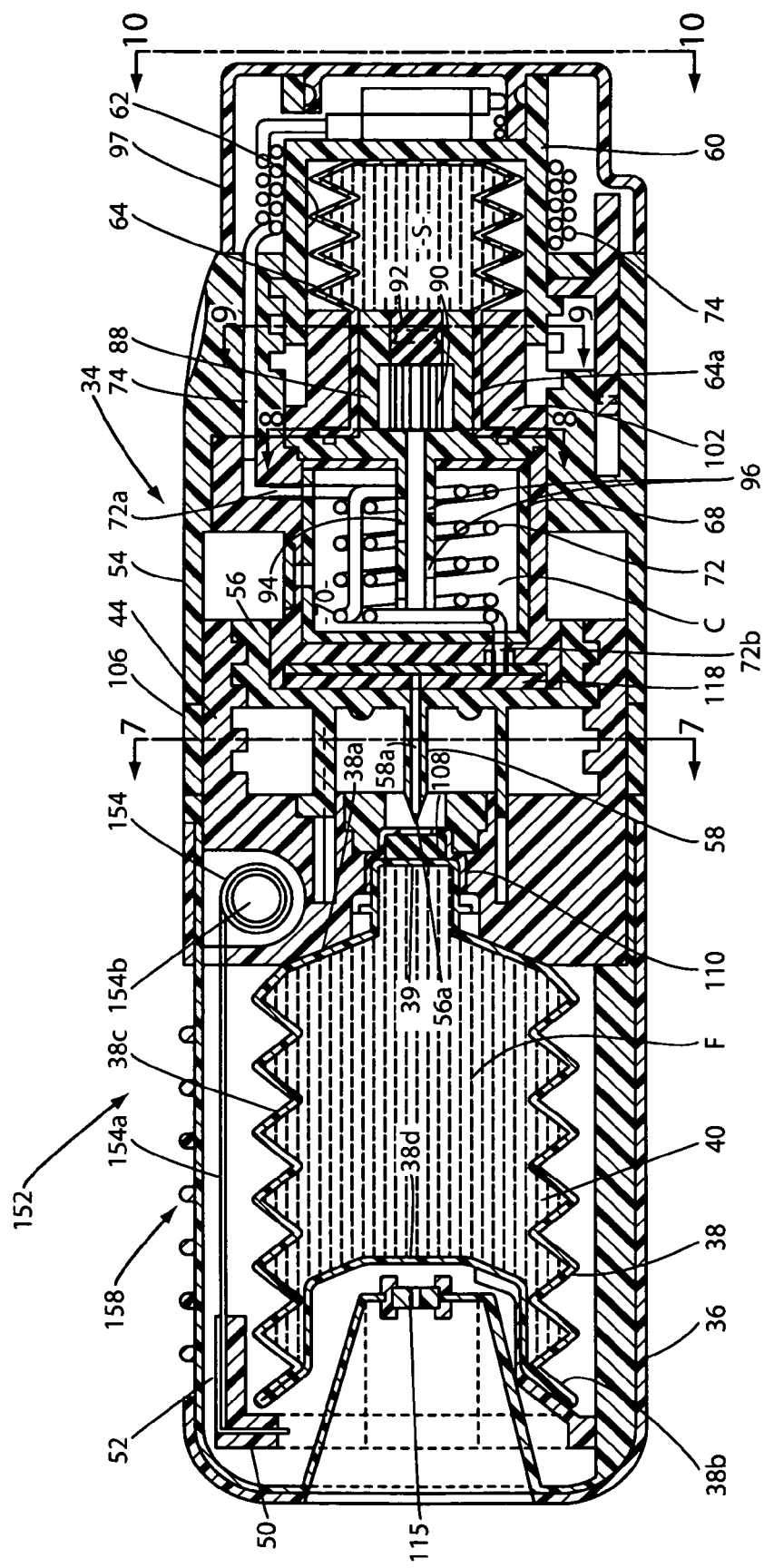
FIG. 35 is a longitudinal cross-sectional view of still another form of the fluid dispensing apparatus of the invention embodying an alternate form of stored energy source in the form of a spring in which the elongated band or strip portion of the spring is coiled about the spring drum in predetermined varying degrees of tightness to produce a spring that exhibits a variation of coil tightness that produces highly specific and desirable linear and non-linear force-distention curves to meet the fluid delivery requirements of the apparatus.

Spring assemblies, such as those depicted in FIGS. 35, 36 and 37 of the drawings, that exhibit a variation of coil tightness that produce highly specific and desirable linear and non-linear force-distention curves to meet the fluid delivery requirements of the invention are available by custom order from various sources, including Vulcan Mfg. & Spring Company of Telford, Pa.

Figure 38:
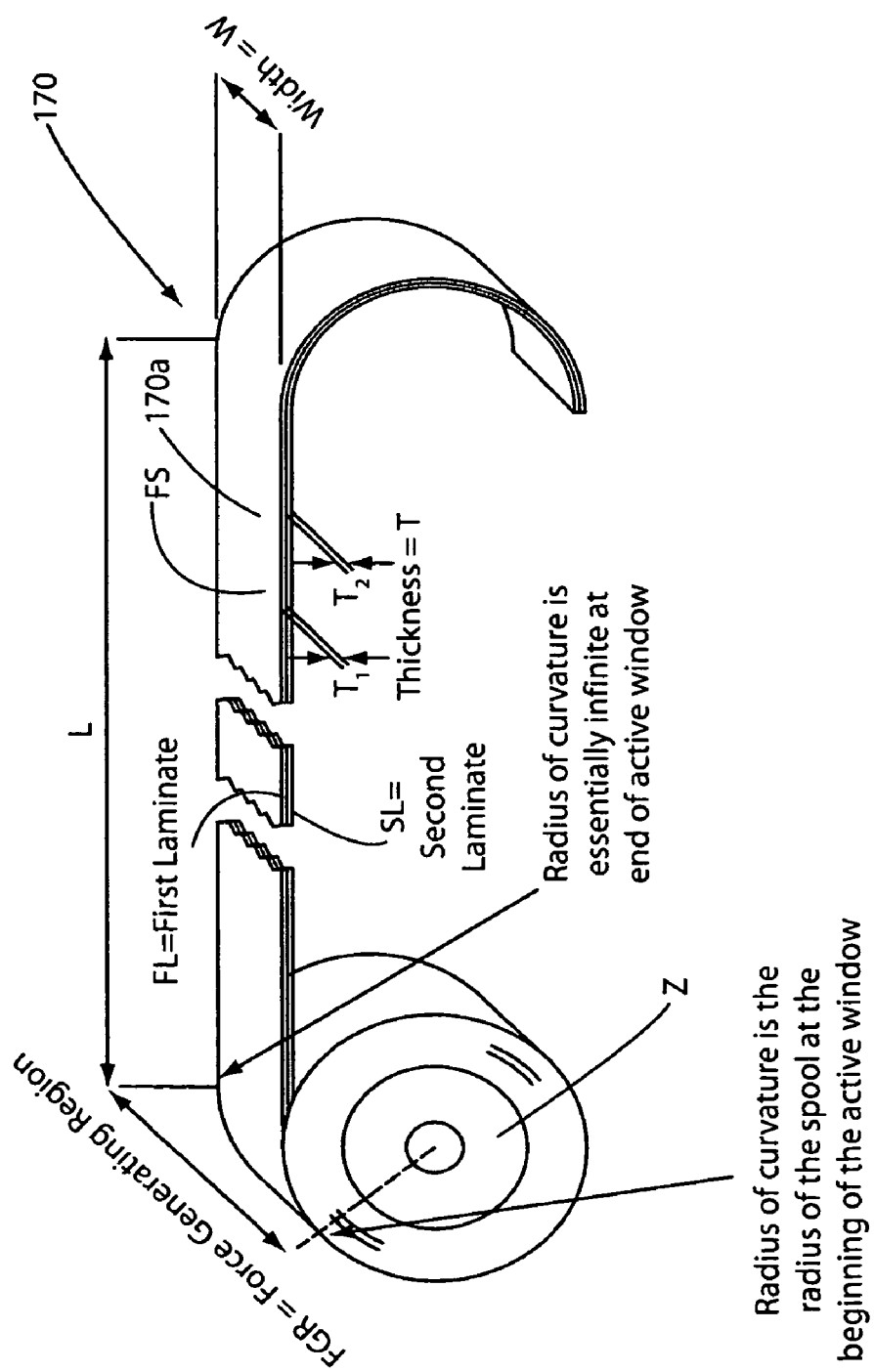
FIG. 38 is a generally perspective view of the retractable spring of yet another modified configuration.

Turning now to FIG. 38 of the drawings, still another form of variable force spring that can be used with the apparatus illustrated in FIG. 35 is there shown. This spring, which is generally identified by the numeral 170, is of a novel laminate construction. This latter form of the retractable spring of a modified configuration is somewhat similar to that previously discussed, but here comprises a novel laminate construction made up of a first laminate FL and a second interconnected laminate SL. As in the spring of FIGS. 35, 36 and 37, the elongated band or strip portion 170a of the spring is coiled about a spring drum Z in predetermined varying degrees of tightness. Accordingly, like the earlier described variable force springs in which the elongated band or strip portion of the spring has been modified to exhibit a cross-sectional mass that varies along the length of the band, springs with a variation of coil tightness, such as illustrated in FIGS. 36 and 37 can produce highly specific and desirable linear and non-linear force-distention curves to meet the fluid delivery requirements of the invention. As before, this type of "interwound negative gradient" spring has no slot. In fact, the winding process is done precisely to create a "negative gradient" so that as the spring retracts, it provides a higher force. Laminate springs with a variation of coil tightness that produce highly specific and desirable linear and non-linear force-distention curves to meet the fluid delivery requirements of the invention are also available by custom order from various sources, including Vulcan Mfg. & Spring Company of Telford, Pa.

The operation of this latest form of the apparatus of the invention is previously illustrated and described embodiments of the invention are substantially identical to that previously described.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An apparatus for dispensing medicaments to a patient comprising:

(a) reservoir assembly comprising:

(i) a reservoir housing;

(ii) an integrally formed, hermetically sealed collapsible container having a fluid reservoir for containing a medicinal fluid disposed within said reservoir housing, said collapsible container including a front portion, a rear portion and a collapsible accordion-like, continuous, uninterrupted side wall that interconnects said front and rear portions, said front portion of said collapsible container including a closure wall and said rear portion of said collapsible container including an inwardly extending ullage segment;

(iii) an internally threaded spring housing connected to said reservoir housing; and (iv) stored energy means mounted within said spring housing for controllably collapsing said sealed container to expel the medicinal fluid there from, said stored energy means comprising a variable force spring assembly; and (b) a temperature altering assembly connected to said reservoir assembly, said temperature altering assembly comprising:

(i) an internally threaded outer shell;

(ii) an externally threaded reservoir piercing housing threadably connected to said spring housing of said reservoir assembly, said reservoir piercing housing including a piercing member for piercing said closure wall of said collapsible container, said piercing member having a fluid passageway;

(iii) an externally threaded control knob threadably connected to said internally threaded outer shell for movement between a first retracted position and a second position, said control knob having an interior chamber; and (iv) a fluid containing bellows disposed within said chamber of said control knob, said fluid containing bellows containing a solution and having a cylindrically shaped neck portion;

(v) a chemical component housing carried within said outer shell intermediate said reservoir piercing housing and control knob, said chemical component housing having an internal chamber containing a chemical component, which upon being mixed with said solution contained within said fluid containing bellows produces a chemical reaction;

(vi) a fluid delivery member disposed within said internal chamber of said chemical component housing, said fluid delivery member being in communication with said passageway of said piercing member;

(vii) an administration line connected to said fluid delivery member;

(viii) a seal plug housing disposed within said cylindrically shaped neck portion of said fluid containing bellows said seal plug housing having a hollow body portion and a flange portion connected to said hollow body portion, said hollow body portion having a plurality of circumferentially spaced bypass flow channels;

(ix) a seal plug carried within said hollow body portion of said seal plug housing for movement between a first retracted position and a second position; and (x) a dispersion tube connected to and extending from said flange portion of said seal plug housing, said dispersion tube being disposed in close proximity to said fluid member and having a plurality of longitudinally spaced fluid outlet passageways in communication with said internal chamber of said housing.

2. The apparatus as defined in claim 1 in which said solution contained within said fluid containing bellows of said control knob comprises a solution and in which said chemical component contained within said internal chamber of said heating housing comprises calcium chloride.

3. The apparatus as defined in claim 1 in which said reservoir assembly further includes a carriage housed within said housing of said reservoir assembly, said carriage being operably associated with said container and with said stored energy source and being movable by said stored energy source from a first retracted position to a second advanced position.

4. The apparatus as defined in claim 1, further including a rate control means carried by said reservoir piercing housing for controlling the rate of fluid flow from said fluid reservoir toward the patient, said rate control means comprises a rate control assembly that includes a rate control plate having at least one micro-channel formed therein.

5. The apparatus as defined in claim 1 in which said variable force spring assembly comprises a spring drum and a spring having an elongated pre-stressed strip, said elongated pre-stressed strip portion being coiled about said spring drum in predetermined varying degrees of tightness.

6. The apparatus as defined in claim 1 in which said chemical component contained within said internal chamber of said heating housing comprises an ammonium salt.

7. The apparatus as defined in claim 1 in which said chemical component contained within said internal chamber of said heating housing is selected from a group consisting of calcium chloride, magnesium chloride, zinc sulfate, sodium carbonate, potassium salts, acetone and pentane.

* * * * *